(12) United States Patent
Morita

(10) Patent No.: US 10,957,039 B2
(45) Date of Patent: Mar. 23, 2021

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Junya Morita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 112 days.

(21) Appl. No.: 16/291,661

(22) Filed: Mar. 4, 2019

(65) Prior Publication Data

US 2019/0304088 A1    Oct. 3, 2019

(30) Foreign Application Priority Data

Mar. 30, 2018 (JP) .............................. JP2018-068965

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0091* (2013.01); *A61B 5/743* (2013.01);
(Continued)

(58) Field of Classification Search
None
See application file for complete search history.

(56) References Cited

U.S. PATENT DOCUMENTS

2003/0194115 A1* 10/2003 Kaufhold .............. G06F 19/321
382/128
2008/0075228 A1* 3/2008 Tasaki .................... A61B 6/542
378/37
(Continued)

FOREIGN PATENT DOCUMENTS

JP    2010-253245 A    11/2010
JP    2011-194024 A    10/2011
(Continued)

OTHER PUBLICATIONS

Fujita, et al. "Computer-aided Diagnosis (CAD) in the Field of Breast-cancer Image Diagnosis", Journal of Medical Laboratory Information, Aug. 1, 2006, vol. 23, No:2, pp. 19-26, with partial English translation.
(Continued)

*Primary Examiner* — Shervin K Nakhjavan
(74) *Attorney, Agent, or Firm* — Birch, Stewart, Kolasch & Birch, LLP

(57) ABSTRACT

In a console, a control unit functions as an acquisition unit that acquires a radiographic image of a breast, a derivation unit that derives a mammary gland content rate for each pixel of a breast region in the radiographic image, and a detection unit that detects a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel in a local region around the specific pixel.

18 Claims, 15 Drawing Sheets

(51) Int. Cl.
*G06K 9/32* (2006.01)
*A61B 5/00* (2006.01)
(52) U.S. Cl.
CPC .. *G06K 9/3233* (2013.01); *G06T 2207/10081* (2013.01); *G06T 2207/30068* (2013.01)

(56) References Cited

U.S. PATENT DOCUMENTS

| | | | | |
|---|---|---|---|---|
| 2009/0086891 | A1* | 4/2009 | Ofuji | A61B 6/463 378/37 |
| 2009/0252396 | A1* | 10/2009 | Morita | G06T 5/008 382/132 |
| 2010/0246924 | A1* | 9/2010 | Morita | A61B 5/4872 382/132 |
| 2010/0321404 | A1* | 12/2010 | Fischer | G16H 40/63 345/632 |
| 2011/0229006 | A1* | 9/2011 | Morita | G06T 7/0012 382/132 |
| 2015/0093013 | A1* | 4/2015 | Morita | A61B 6/5205 382/132 |
| 2016/0292851 | A1* | 10/2016 | Hamauzu | G06T 5/002 |
| 2017/0116731 | A1* | 4/2017 | Tsunomori | G06T 7/136 |

FOREIGN PATENT DOCUMENTS

| | | |
|---|---|---|
| JP | 2016-190012 A | 11/2016 |
| VA | WO2008/038525 A1 | 4/2008 |

OTHER PUBLICATIONS

Fujizasa, et al. "Examination of average absorbed dose by the mammary gland using a compressed breast model," Journal of Japanese Breast Cancer Screening Society, Oct. 20, 1997, vol. 6. No. 3, pp. 291-298, with partial English translation.

Office Action dated Jan. 29, 2021 in corresponding Japanese Patent Application No. 2018-068965, with English translation.

* cited by examiner

| MAMMARY GLAND CONTENT RATE (%) | CATEGORY |
|---|---|
| EQUAL TO OR GREATER THAN 0, LESS THAN 25 | I |
| EQUAL TO OR GREATER THAN 25, LESS THAN 50 | II |
| EQUAL TO OR GREATER THAN 50, LESS THAN 75 | III |
| EQUAL TO OR GREATER THAN 75, EQUAL TO OR LESS THAN 100 | IV |

IMAGE PROCESSING APPARATUS, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2018-068965, filed on Mar. 30, 2018. Each of the above application(s) is hereby expressly incorporated by reference, in its entirety, into the present application.

BACKGROUND OF THE INVENTION

1. Field of the Invention

The present disclosure relates to an image processing apparatus, an image processing method, and a non-transitory computer readable recording medium storing an image processing program.

2. Description of the Related Art

In general, an object of interest, such as a breast cancer, in the breast has been diagnosed on the basis of a radiographic image of the breast of a subject captured by a so-called mammography apparatus. However, in the case of the breast with high mammary gland density, an image of the object of interest in the radiographic image may be hidden by the mammary glands and may be difficult to see. Therefore, a technique has been known which derives the content of the mammary glands in order to detect an image of an object of interest from an image of a breast region in a radiographic image. For example, JP2011-194024A discloses a technique that calculates the mammary gland content rate for each pixel of an image of a breast region and determines whether an abnormal shadow is present in each pixel on the basis of the calculated mammary gland content rate.

SUMMARY OF THE INVENTION

However, even though the mammary gland content rate of the entire breast is the same in a case in which the mammary glands are concentrated in some regions of the breast and in a case in which the mammary glands are scattered in the entire breast, the object of interest is more likely to be hidden and is more difficult to see in the case in which the mammary glands are concentrated.

The technique disclosed in JP2011-194024A do not consider the case in which the mammary glands are concentrated in some regions of the breast, which requires attention to the observation of the object of interest, and there is room for improvement.

The present disclosure has been made in view of the above-mentioned problems and an object of the present disclosure is to provide an image processing apparatus, an image processing method, and a non-transitory computer readable recording medium storing an image processing program that can detect a region in which an object of interest needs to be carefully observed in a radiographic image of the breast.

In order to achieve the object, according to a first aspect of the present disclosure, there is provided an image processing apparatus comprising: an acquisition unit that acquires a radiographic image of a breast; a derivation unit that derives a mammary gland content rate for each pixel of a breast region in the radiographic image; and a detection unit that detects a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel around the specific pixel.

According to a second aspect of the present disclosure, in the image processing apparatus according to the first aspect, the detection unit may derive a representative value of a mammary gland content rate of a local region which includes the specific pixel and has a predetermined size smaller than that of the breast region and specifies the specific pixel, of which a representative value of the mammary gland content rate is equal to or greater than a predetermined threshold value, in the local region as a pixel included in the mammary gland concentrated region.

According to a third aspect of the present disclosure, in the image processing apparatus according to the second aspect, the size of the local region may be determined according to a size of an object of interest to be observed.

According to a fourth aspect of the present disclosure, in the image processing apparatus according to the third aspect, the size of the local region may be larger than the size of the object of interest.

In order to achieve the object, according to a fifth aspect of the present disclosure, there is provided an image processing apparatus comprising: an acquisition unit that acquires a radiographic image of a breast; a derivation unit that derives a mammary gland content rate for each pixel of a breast region in the radiographic image; and a detection unit that detects a region in which a predetermined number or more of pixels whose mammary gland content rate is equal to or greater than a predetermined threshold value are adjacent to each other as a mammary gland concentrated region in which mammary glands are concentrated in the breast region.

According to a sixth aspect of the present disclosure, in the image processing apparatus according to any one of the first to fifth aspects, the detection unit may derive a representative value of a mammary gland content rate of the mammary gland concentrated region and output the representative value.

According to a seventh aspect of the present disclosure, the image processing apparatus according to any one of the first to sixth aspects may further comprise a display control unit that performs control such that a category corresponding to the breast is specified from categories into which the breasts are classified according to the mammary gland content rate on the basis of the representative value of the mammary gland content rate of the mammary gland concentrated region and is displayed on a display unit.

According to an eighth aspect of the present disclosure, the image processing apparatus according to any one of the first to sixth aspects may further comprise a display control unit that performs control such that a category corresponding to the breast is specified from categories into which the breasts are classified according to the mammary gland content rate of the entire breast region and the mammary gland content rate of the entire mammary gland concentrated region, on the basis of the representative value of the mammary gland content rate of the mammary gland concentrated region and the mammary gland content rate of the entire breast region and is displayed on a display unit.

According to a ninth aspect of the present disclosure, the image processing apparatus according to any one of the first to sixth aspects may further comprise a display control unit that performs control such that at least one of a first category which corresponds to the breast and is specified from categories into which the breasts are classified according to the mammary gland content rate on the basis of the representative value of the mammary gland content rate of the mammary gland concentrated region or a second category which corresponds to the breast and is specified from the categories into which the breasts are classified according to the mammary gland content rate on the basis of a mammary gland content rate of the entire breast region is displayed on a display unit.

According to a tenth aspect of the present disclosure, the image processing apparatus according to any one of the first to sixth aspects may further comprise a display control unit that performs control such that the mammary gland content rate of the entire breast region and the mammary gland content rate of the entire mammary gland concentrated region are displayed on a display unit.

According to an eleventh aspect of the present disclosure, the image processing apparatus according to the tenth aspect may further comprise a receiving unit that receives a selection of a mammary gland content rate to be displayed from the mammary gland content rate of the entire breast region and the mammary gland content rate of the entire mammary gland concentrated region. The display control unit may perform control such that at least one of the mammary gland content rate of the entire breast region or the mammary gland content rate of the entire mammary gland concentrated region is displayed in response to the selection received by the receiving unit.

According to a twelfth aspect of the present disclosure, the image processing apparatus according to any one of the first to sixth aspects may further comprise a display control unit that performs control such that a result of comparison between a statistical value indicating a correspondence relationship between at least one of age or a thickness of the breast and the mammary gland content rate and the representative value of the mammary gland content rate of the mammary gland concentrated region is displayed on a display unit.

According to a thirteenth aspect of the present disclosure, the image processing apparatus according to any one of the first to sixth aspects may further comprise a display control unit that performs control such that the mammary gland concentrated region detected by the detection unit is displayed on a display unit so as to be highlighted.

According to a fourteenth aspect of the present disclosure, in the image processing apparatus according to the thirteenth aspect, the display control unit may perform control such that information indicating the mammary gland content rate of each pixel of the breast region derived by the derivation unit is further displayed on the display unit.

According to a fifteenth aspect of the present disclosure, the image processing apparatus according to any one of the first to fourteenth aspects may further comprise a warning unit that issues a warning indicating that the mammary gland content rate of the breast region is high in a case in which the representative value of the mammary gland content rate of the mammary gland concentrated region is equal to or greater than a predetermined threshold value.

According to a sixteenth aspect of the present disclosure, in the image processing apparatus according to any one of the first to fifteenth aspects, the radiographic image acquired by the acquisition unit may be a two-dimensional image that is captured by a radiation detector of a mammography apparatus. The image processing apparatus may further comprise a command unit that outputs, to the mammography apparatus, a command to irradiate the breast with radiation emitted from a radiation source at a plurality of different irradiation angles to capture a plurality of projection images in a case in which the mammary gland content rate of the entire mammary gland concentrated region detected by the detection unit is equal to or greater than a threshold value.

According to a seventeenth aspect of the present disclosure, in the image processing apparatus according to any one of the first to fifteenth aspects, the radiographic image acquired by the acquisition unit may be a plurality of projection images captured by a mammography apparatus by irradiating the breast with radiation emitted from a radiation source at a plurality of different irradiation angles, or the plurality of projection images and a two-dimensional image of the breast captured by the mammography apparatus. The image processing apparatus may further comprise: a generation unit that generates a series of tomographic images from the plurality of projection images; and a display speed control unit that performs control such that the series of tomographic images is continuously displayed on the display unit at a first speed in a case in which the mammary gland content rate of the entire mammary gland concentrated region detected by the detection unit is less than a threshold value and performs control such that the series of tomographic images is continuously displayed on the display unit at a second speed lower than the first speed in a case in which the mammary gland content rate of the entire mammary gland concentrated region is equal to or greater than the threshold value.

In order to achieve the object, according to an eighteenth aspect of the present disclosure, there is provided an image processing method comprising: acquiring a radiographic image of a breast; deriving a mammary gland content rate for each pixel of a breast region in the radiographic image; and detecting a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel around the specific pixel.

In order to achieve the object, according to a nineteenth aspect of the present disclosure, there is provided an image processing method comprising: acquiring a radiographic image of a breast; deriving a mammary gland content rate for each pixel of a breast region in the radiographic image; and detecting a region in which a predetermined number or more of pixels whose mammary gland content rate is equal to or greater than a predetermined threshold value are adjacent to each other as a mammary gland concentrated region in which mammary glands are concentrated in the breast region.

In order to achieve the object, according to a twentieth aspect of the present disclosure, there is provided a non-transitory computer readable recording medium storing an image processing program that causes a computer to perform: acquiring a radiographic image of a breast; deriving a mammary gland content rate for each pixel of a breast region in the radiographic image; and detecting a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel around the specific pixel.

In order to achieve the object, according to a twenty-first aspect of the present disclosure, there is provided a non-transitory computer readable recording medium storing an image processing program that causes a computer to perform: acquiring a radiographic image of a breast; deriving a mammary gland content rate for each pixel of a breast region in the radiographic image; and detecting a region in which a predetermined number or more of pixels whose mammary gland content rate is equal to or greater than a predetermined threshold value are adjacent to each other as a mammary gland concentrated region in which mammary glands are concentrated in the breast region.

According to the present disclosure, it is possible to detect a region in which an object of interest needs to be carefully observed in a radiographic image of the breast.

DESCRIPTION OF THE PREFERRED EMBODIMENTS

Hereinafter, embodiments of the invention will be described in detail with reference to the drawings. The embodiments do not limit the invention.

First Embodiment

Figure 1:
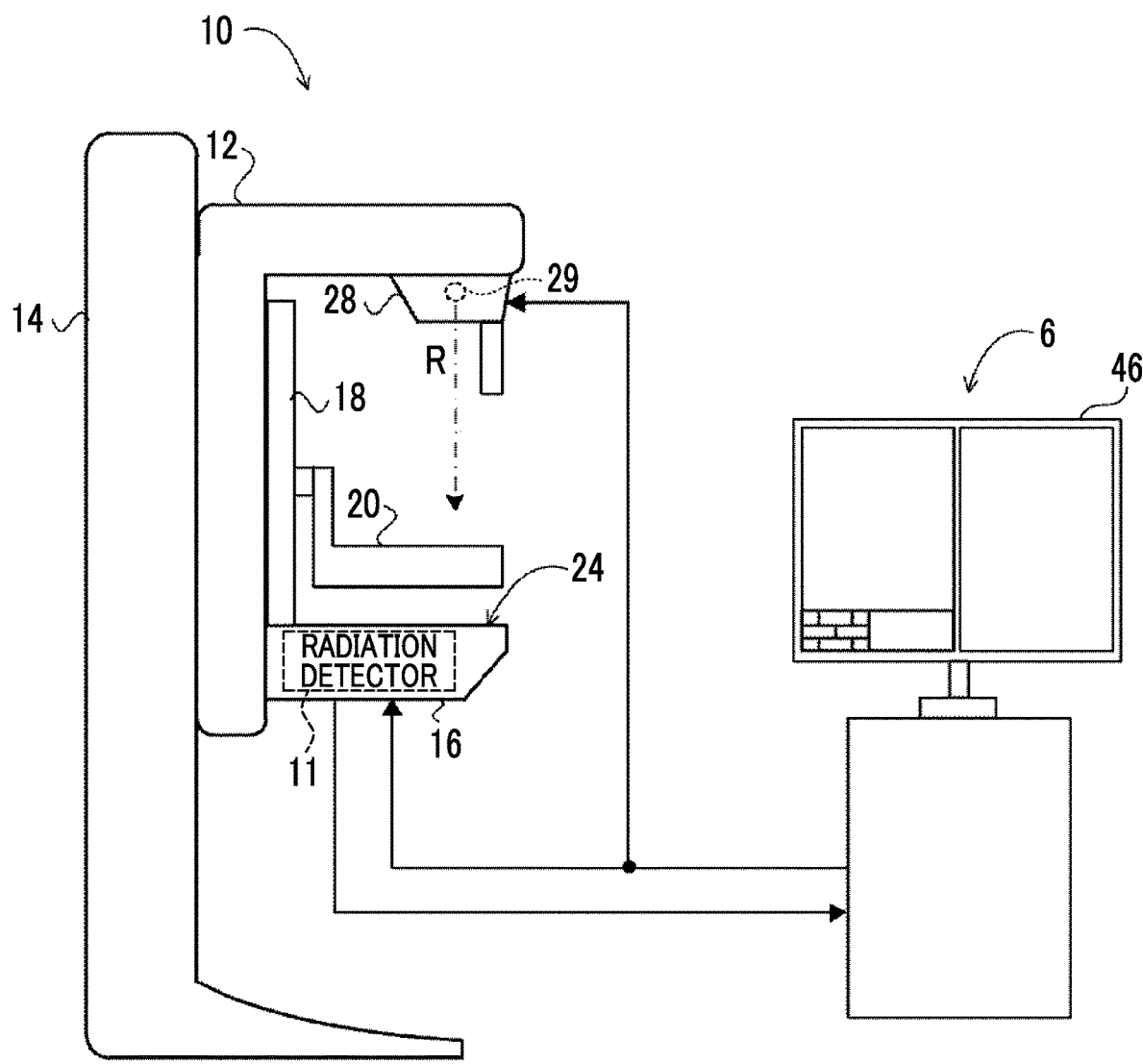
FIG. 1 is a diagram illustrating an example of the overall configuration of a radiography system according to a first embodiment.

First, an example of the overall configuration of a radiography system according to this embodiment will be described. FIG. 1 is a configuration diagram illustrating an example of the overall configuration of a radiography system 1 according to this embodiment.

The radiography system 1 according to this embodiment has a function of capturing radiographic images in response to an operation of a user, such as a doctor or a radiology technician, on the basis of a command (imaging order) input from an external system (for example, a radiology information system (RIS)) through a console 6.

Figure 2:
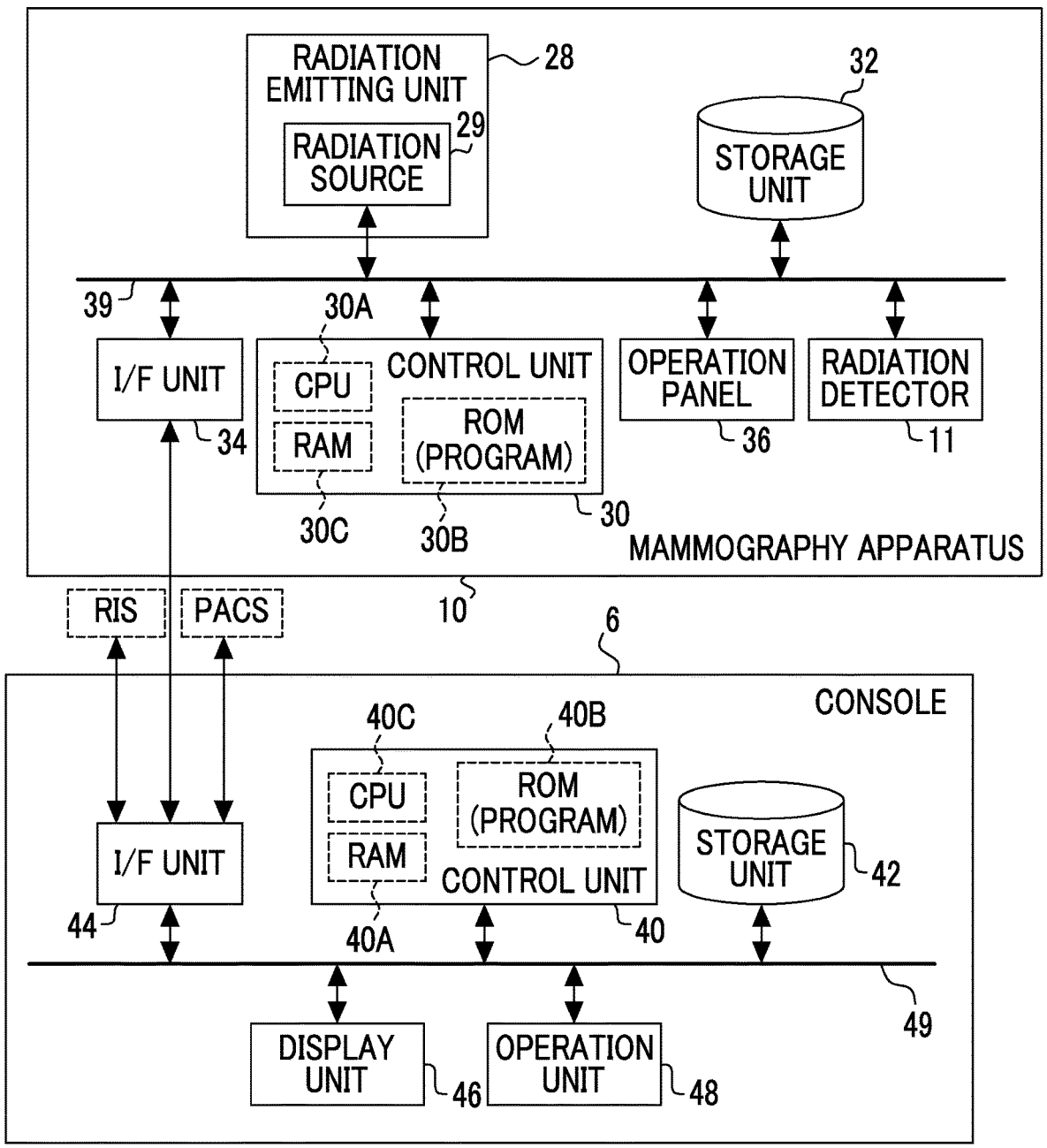
FIG. 2 is a block diagram illustrating an example of the configuration of a console and a mammography apparatus according to the first embodiment.

As illustrated in FIG. 1, the radiography system 1 according to this embodiment includes the console 6 and a mammography apparatus 10. FIG. 2 is a block diagram illustrating an example of the configuration of the console 6 and the mammography apparatus 10 according to this embodiment.

The console 6 according to this embodiment has a function of controlling the mammography apparatus 10 using, for example, an imaging order or various kinds of information acquired from an external system through a wireless communication local area network (LAN). The console 6 according to this embodiment is an example of an image processing apparatus according to the present disclosure.

For example, the console 6 according to this embodiment is a server computer. As illustrated in FIG. 2, the console 6 includes a control unit 40, a storage unit 42, an interface (I/F) unit 44, a display unit 46, and an operation unit 48. The control unit 40, the storage unit 42, the I/F unit 44, the display unit 46, and the operation unit 48 are connected to each other through a bus 49, such as a system bus or a control bus, such that they can transmit and receive various kinds of information.

The control unit 40 according to this embodiment controls the overall operation of the console 6. The control unit 40 according to this embodiment includes a central processing unit (CPU) 40A, a read only memory (ROM) 40B, and a random access memory (RAM) 40C. For example, various programs including a mammary gland concentrated region detection processing program and a radiographic image display processing program (which will be described below)

executed by the CPU 40A are stored in the ROM 40B in advance. The RAM 40C temporarily stores various kinds of data.

For example, the image data of a radiographic image captured by the mammography apparatus 10 and various other kinds of information are stored in the storage unit 42. Examples of the storage unit 42 include a hard disk drive (HDD) and a solid state drive (SSD). The I/F unit 44 transmits and receives various kinds of information to and from the mammography apparatus 10 or external systems, such as an RIS and a picture archiving and communication system (PACS), using at least one of wireless communication or wired communication.

The display unit 46 displays, for example, information related to imaging and the captured radiographic image. The operation unit 48 is used by a user to input, for example, a command to capture a radiographic image and a command related to image processing for the captured radiographic image. For example, the operation unit 48 may have the form of a keyboard or various types of switches or the form of a touch panel integrated with the display unit 46.

The mammography apparatus 10 according to this embodiment is an apparatus that irradiates the breast of a subject, which is an object, with radiation R (X-rays) to capture the radiographic image of the breast. As illustrated in FIG. 1, the mammography apparatus 10 comprises an imaging unit 12 and a base portion 14 that supports the imaging unit 12.

The imaging unit 12 comprises an imaging table 16 having a planar imaging surface 24 that come into contact with the breast of the subject, a compression plate 20 that compresses the breast against the imaging surface 24 of the imaging table 16, and a holding portion 18 that supports the imaging table 16 and the compression plate 20. In addition, a member that transmits the radiation R is used as the compression plate 20.

The holding portion 18 supports the imaging table 16 and a radiation source 29 such that the imaging surface 24 and the radiation source 29 are separated by a predetermined distance. In addition, the holding portion 18 holds the compression plate 20 such that the compression plate 20 is slid to change the distance between the compression plate 20 and the imaging surface 24.

In a case in which the mammography apparatus 10 captures the radiographic image of the breast of the subject, for example, a radiology technician positions the subject and the breast placed on the imaging surface 24 of the imaging table 16 is compressed between the compression plate 20 and the imaging surface 24 and is fixed.

A radiation detector 11 that detects the radiation R transmitted through the breast and the imaging surface 24 is provided in the imaging table 16. A radiographic image is generated on the basis of the radiation R detected by the radiation detector 11. However, the type of radiation detector 11 according to this embodiment is not particularly limited. For example, the radiation detector 11 may be an indirect-conversion-type radiation detector that converts the radiation R into light and converts the converted light into charge or a direct-conversion-type radiation detector that directly converts the radiation R into charge. In this embodiment, image data indicating the radiographic image output from the radiation detector 11 of the mammography apparatus 10 is transmitted to the console 6.

As illustrated in FIG. 2, the mammography apparatus 10 according to this embodiment includes the radiation detector 11, a radiation emitting unit 28 including the radiation source 29, a control unit 30, a storage unit 32, an I/F unit 34, and an operation panel 36. The radiation detector 11, the radiation emitting unit 28, the control unit 30, the storage unit 32, the I/F unit 34, and the operation panel 36 are connected to each other through a bus 39, such as a system bus or a control bus, such that they can transmit and receive various kinds of information.

The control unit 30 according to this embodiment controls the overall operation of the mammography apparatus 10. In addition, in a case in which a radiographic image is captured, the control unit 30 according to this embodiment controls the radiation detector 11 and the radiation emitting unit 28. The control unit 30 according to this embodiment comprises a CPU 30A, a ROM 30B, and a RAM 30C. For example, various programs including a program for controlling the capture of a radiographic image which are executed by the CPU 30A are stored in the ROM 30B in advance. The RAM 30C temporarily stores various kinds of data.

For example, the image data of the radiographic image captured by the radiation detector 11 and various other kinds of information are stored in the storage unit 32. Examples of the storage unit 32 include an HDD and an SSD. The I/F unit 34 transmits and receives various kinds of information to and from the console 6 using wireless communication or wired communication. For example, the operation panel 36 is provided as a plurality of switches in the imaging table 16 of the mammography apparatus 10. In addition, the operation panel 36 may be provided as a touch panel.

Next, the operation of the console 6 in the radiography system 1 according to this embodiment will be described. The console 6 according to this embodiment has a function which detects a region (hereinafter, referred to as a "mammary gland concentrated region") in which the mammary glands are concentrated in the breast from the radiographic image of the breast captured by the mammography apparatus 10 and derives the mammary gland content rate of the mammary gland concentrated region. In addition, the mammary gland content rate means the volume ratio of mammary gland tissues in each region. That is, the mammary gland content rate indicates the content of the mammary glands in a thickness direction of the breast which is the emission direction of the radiation R. In a case in which there is no mammary gland and only fat is present, the mammary gland content rate is 0. As the density of mammary glands increases, the mammary gland content rate increases.

In the console 6 according to this embodiment, for example, in a case in which a command to display a radiographic image is received from the user through the operation unit 48 of the console 6, a mammary gland concentrated region detection process for detecting the mammary gland concentrated region from the radiographic image and a radiographic image display process for displaying the radiographic image are sequentially performed.

Figure 3:
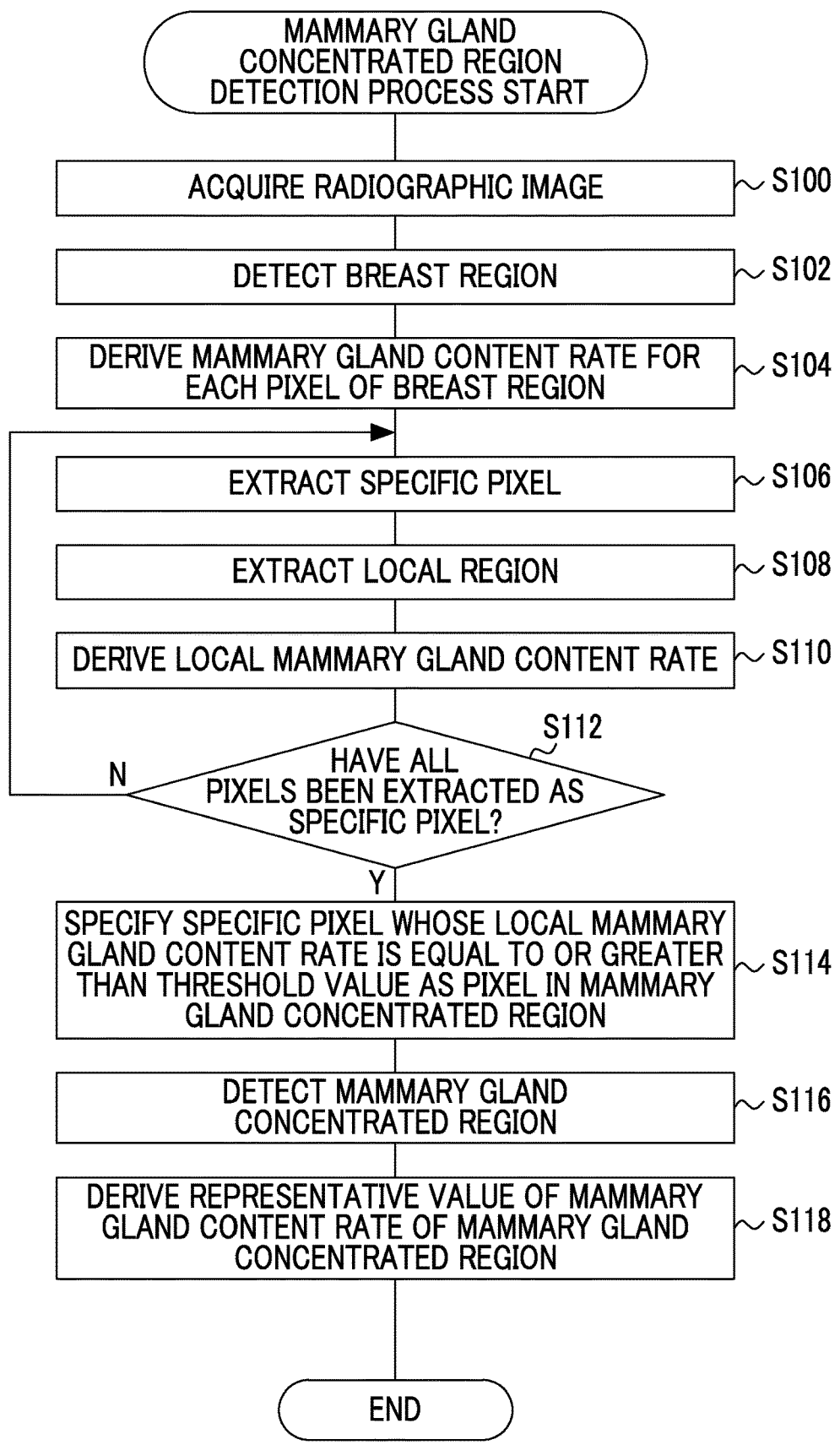
FIG. 3 is a flowchart illustrating an example of the flow of a mammary gland concentrated region detection process performed by the console according to the first embodiment.
Figure 4:
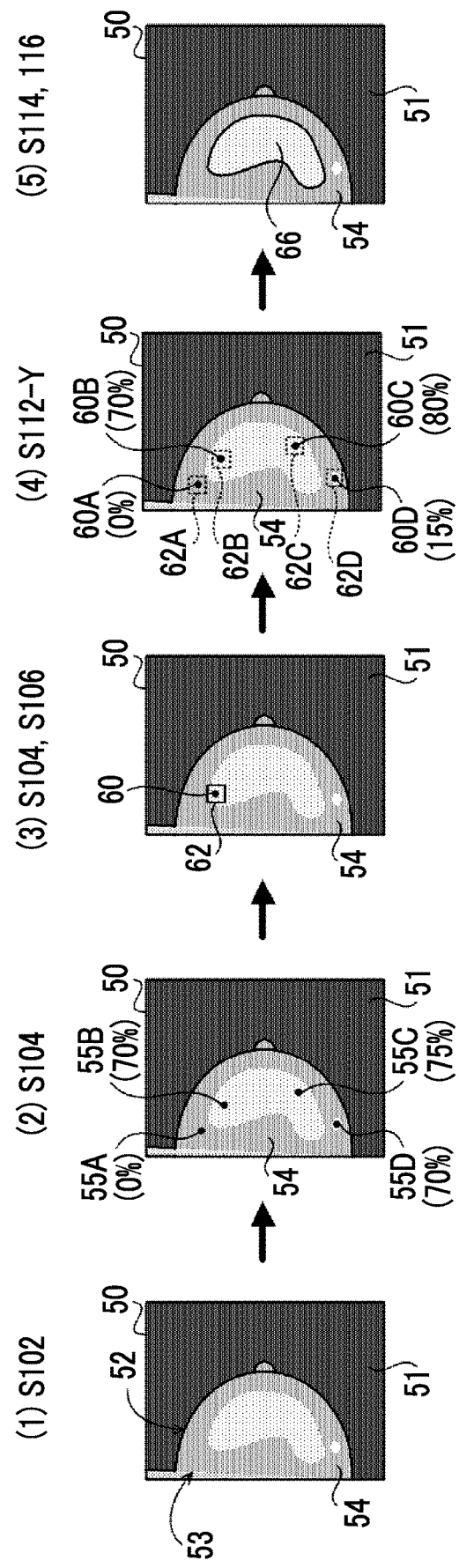
FIG. 4 is a diagram illustrating the mammary gland concentrated region detection process performed by the console according to the first embodiment.

First, the operation of the mammary gland concentrated region detection process by the console 6 according to this embodiment will be described with reference to FIGS. 3 and 4. FIG. 3 is a flowchart illustrating an example of the flow of the mammary gland concentrated region detection process performed by the control unit 40 of the console 6 according to this embodiment. FIG. 4 is a diagram illustrating an example of the mammary gland concentrated region detection process illustrated in FIG. 3.

In the console 6 according to this embodiment, for example, in a case in which a command to display a radiographic image is received from the user through the operation unit 48 of the console 6, the CPU 40A of the control unit 40 executes the mammary gland concentrated region detection processing program stored in the ROM 40B to perform the mammary gland concentrated region detection process illustrated in FIG. 3. In a case in which the mammary gland concentrated region detection process is performed, the control unit 40 functions as an example of an acquisition unit, a derivation unit, and a detection unit according to the present disclosure.

As illustrated in FIG. 3, in Step S100, the control unit 40 acquires a radiographic image 50 to be displayed. The acquisition destination of the radiographic image 50 is not particularly limited and may be any apparatus that stores the desired radiographic image 50. In addition, the acquisition destination of the radiographic image 50 may be the mammography apparatus 10, the storage unit 42 of the console, and a PACS.

Then, in Step S102, the control unit 40 detects a breast region 54 indicating the breast of the subject from the acquired radiographic image 50 (see (1) of FIG. 4). A method for detecting the breast region 54 from the radiographic image 50 in the control unit 40 is not particularly limited and various known methods can be applied. For example, as illustrated in (1) of FIG. 4, the control unit 40 may detect a breast skin line 52 and a boundary 53 between the breast and the pectoralis major from the radiographic image 50 and detect a region surrounded by the detected boundary 53 and the detected breast skin line 52 as the breast region 54.

Then, in Step S104, the control unit 40 derives the mammary gland content rate for each pixel of the breast region 54 (see (2) of FIG. 4). A method for deriving the mammary gland content rate for each pixel of the breast region 54 in the control unit 40 is not particularly limited and various known methods can be applied.

For example, the control unit 40 may apply the technique disclosed in JP2010-253245A to calculate mammary gland content rate r(x, y)(%) represented by the following Expression (1):

$$r(x, y) = \frac{A(x, y) - I(x, y)}{I_0 - A(x, y)} \times \frac{1}{\mu - 1}. \quad (1)$$

In Expression (1), $I_0$ indicates a pixel value of a region without an object, that is, a directly irradiated region 51, A(x, y) indicates a pixel value of a fat pixel, I(x, y) indicates a value of a pixel from which the mammary gland content rate r(x, y) is derived, and μ indicates an average attenuation coefficient ratio of the mammary gland to fat (an average attenuation coefficient of the mammary gland/an average attenuation coefficient of fat). In this embodiment, the average attenuation coefficient ratio μ is stored in, for example, the storage unit 42 in advance.

The fat pixel value A(x, y) is derived by, for example, the technique disclosed in JP2005-65855A or JP2010-253245A. The technique disclosed in, for example, JP2005-65855A or JP2010-253245A separates the mammary glands from a fat region on the basis of a threshold value that is derived from the pixel value of the pectoralis major close to the chest wall and the fat region in the vicinity of the pectoralis major in the breast region 54 and derives the fat pixel value A (x, y) at the position of the pixel (x, y) in the fat region.

A mammary gland content rate map for each pixel (hereinafter, referred to as a "pixel unit mammary gland content rate map") in which the mammary gland content rate is derived for each pixel of the entire breast region 54 is created by the process in this step. For example, (2) of FIG. 4 illustrates a state in which the pixel unit mammary gland content rate map in which, among the pixels of the breast region 54, the mammary gland content rate of a pixel 55A is 0%, the mammary gland content rate of a pixel 55B is 70%, the mammary gland content rate of a pixel 55C is 75%, and the mammary gland content rate of a pixel 55D is 70% is created.

Then, in Step S106, the control unit 40 extracts a specific pixel 60 from the pixels of the breast region 54 (see (3) of FIG. 4). Then, in Step S108, the control unit 40 extracts a local region 62 having the extracted specific pixel 60 as the center (see (3) of FIG. 4).

In this embodiment, the size of the local region 62 is determined according to the size of the object of interest to be observed, for example, in consideration of the size of a hidden portion of the object of interest. For example, in a case in which the object of interest is an initial breast cancer, the size of the object of interest is equal to or less than 2 cm. The console 6 according to this embodiment assumes the initial breast cancer as the object of interest and predetermines the size of the local region 62 to be 2 cm×2 cm. In addition, the size of the local region 62 is not limited to this embodiment. In a case in which the size of the local region 62 is too large, the accuracy of detecting the boundary line of the mammary gland concentrated region is reduced. It is preferable that the size of the local region 62 is smaller than the size of the breast region 54 and is slightly larger than the size of the object of interest. The specific size may be obtained by experiments in advance according to, for example, the size and type of the object of interest. For example, the size of the local region 62 may be stored so as to be associated with each type of the object of interest and the size of the local region 62 corresponding to the object of interest instructed by the user through the operation unit 48 may be applied.

Then, in Step S110, the control unit 40 derives a representative value (hereinafter, referred to as a "local mammary gland content rate") of the mammary gland content rate of the local region 62. The control unit 40 according to this embodiment derives the average value of the mammary gland content rate of each pixel of the local region 62 as the local mammary gland content rate. The derived local mammary gland content rate is associated with the specific pixel 60 included in the local region 62 which is a derivation target. The local mammary gland content rate which is the representative value of the mammary gland content rate of the local region 62 is not limited to the average value and may be other statistics, such as a mean, a median, and a mode, except a maximum value and a minimum value.

Then, in Step S112, the control unit 40 determines whether all of the pixels of the breast region 54 have been extracted as the specific pixel 60 by the process in Step S106. In a case in which there is a pixel which has not been extracted as the specific pixel 60 among the pixels of the breast region 54, the determination result in Step S112 is "No" and the process returns to Step S106. The process in Steps S108 and S110 is repeated. On the other hand, in a case in which all of the pixels of the breast region 54 have been extracted as the specific pixel 60, the determination result in Step S112 is "Yes" and the process proceeds to Step S114. In this case, a mammary gland content rate map (Hereinafter, referred to as a "local unit mammary gland content rate map") for each specific pixel 60 (each local region 62) has been created. For example, (4) of FIG. 4 illustrates a state in which the local unit mammary gland content rate map in which, among the specific pixels 60 of the breast region 54, the mammary gland content rate of a specific pixel 60A (local region 62A) is 0%, the mammary gland content rate of a specific pixel 60B (local region 62B) is 70%, the mammary gland content rate of a specific pixel 60C (local region 62C) is 80%, and the mammary gland content rate of a specific pixel 60D (local region 62D) is 15% has been created.

As can be seen from the comparison between (2) and (4) of FIG. 4, the mammary gland content rate of the same pixel (position) may be different in the pixel unit mammary gland content rate map and the local unit mammary gland content rate map.

In Step S114, the control unit 40 specifies the specific pixel 60, of which the associated local mammary gland content rate is equal to or greater than a threshold value, as a pixel of a mammary gland concentrated region 66 (see (5) of FIG. 4). In addition, a threshold value for specifying the mammary gland concentrated region 66 may be determined according to the mammary gland content rate that is generally diagnosed as a high-density breast, that is, a so-called dense breast, or the mammary gland content rate instructed by the user through, for example, the operation unit 48 may be applied.

Then, in Step S116, the control unit 40 detects the mammary gland concentrated region 66 on the basis of the specification result in Step S114 (see (5) of FIG. 4).

Then, in Step S118, the control unit 40 derives a representative value (hereinafter, referred to as a "mammary gland content rate in the mammary gland concentrated region") of the mammary gland content rate of the detected mammary gland concentrated region 66 and then ends the mammary gland concentrated region detection process. The control unit 40 according to this embodiment derives the average value of the mammary gland content rate of each pixel in the mammary gland concentrated region 66 as an example of the mammary gland content rate in the mammary gland concentrated region. In addition, the mammary gland content rate in the mammary gland concentrated region which is the representative value of the mammary gland content rate of the mammary gland concentrated region 66 is not limited to the average value and may be other statistics, such as a mean, a median, and a mode, except a maximum value and a minimum value. In (5) of FIG. 4, the case in which one mammary gland concentrated region 66 is detected is given as an example. However, a plurality of mammary gland concentrated regions 66 may be detected by the process in Step S116. In this case, one mammary gland content rate (representative value) in the mammary gland concentrated region may be derived for all of the plurality of mammary gland concentrated regions 66. Alternatively, the mammary gland content rate (representative value) in the mammary gland concentrated region may be derived for each of the plurality of mammary gland concentrated regions 66. Any of the configurations can be used.

Figure 5:
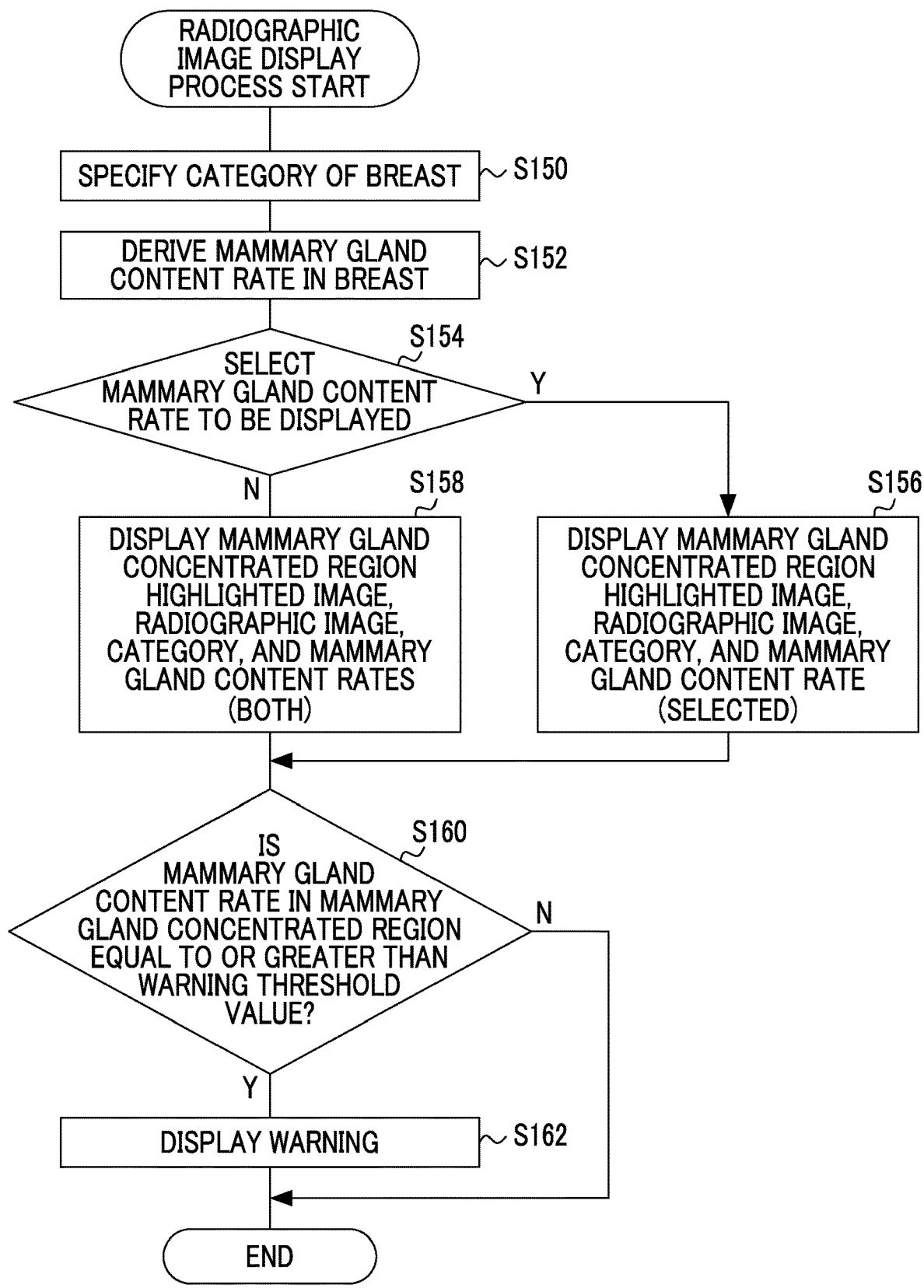
FIG. 5 is a flowchart illustrating an example of the flow of a radiographic image display process performed by the console according to the first embodiment.

In a case in which the mammary gland concentrated region detection process illustrated in FIG. 3 ends, the control unit 40 according to this embodiment performs the radiographic image display process for displaying a radiographic image on the display unit 46. FIG. 5 is a flowchart illustrating an example of the flow of the radiographic image display process performed by the control unit 40 of the console 6 according to this embodiment.

In the console 6 according to this embodiment, for example, in a case in which the mammary gland concentrated region detection process (see FIG. 3) ends, the CPU 40A of the control unit 40 executes the radiographic image display processing program stored in the ROM 40B to perform the radiographic image display process illustrated in FIG. 5. In a case in which the radiographic image display process is performed, the control unit 40 functions as an example of a display control unit, a receiving unit, and a warning unit according to the present disclosure.

Figures 6, 7:
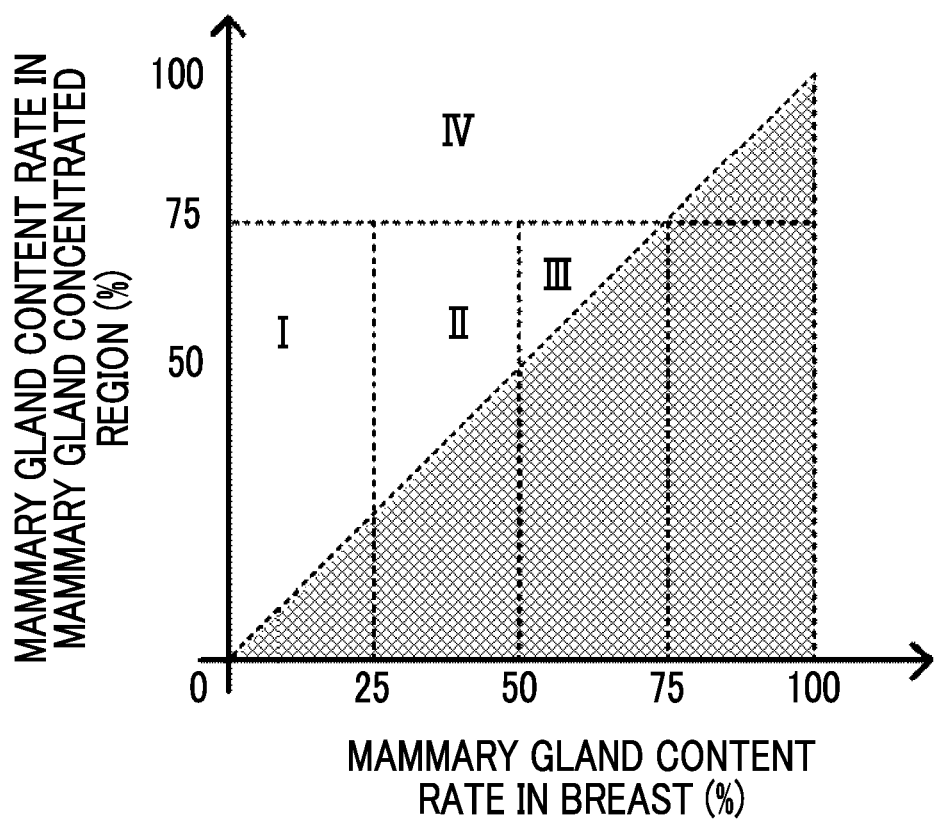
FIG. 6 is a diagram illustrating an example of categories into which the breasts are classified according to mammary gland content rate.
FIG. 7 is a diagram illustrating an example of categories into which the breasts are classified according to mammary gland content rate in the breast and mammary gland content rate in the mammary gland concentrated region.

In Step S150, the control unit 40 specifies a category, to which the breast which is an object belongs, on the basis of the mammary gland content rate in the mammary gland concentrated region derived in Step S118 of the mammary gland concentrated region detection process. Here, the category indicates a classification corresponding to the mammary gland content rate. FIG. 6 illustrates an example of the categories into which the breasts are classified according to the mammary gland content rate as the classification corresponding to the mammary gland content rate. In the example illustrated in FIG. 6, categories I to IV are given according to the mammary gland content rate. In the classification illustrated in FIG. 6, as the mammary gland content rate increases, a value indicating the category increases. In addition, this category classification may correspond to, for example, classification into "fatty", "mammary gland diffuseness", "non-uniform high density", and "(very) high density" represented by the mammography guidelines. For example, the mammary gland content rate which is a threshold value for each category may be set and changed by the user through the operation unit 48.

FIG. 7 illustrates an example of the categories into which the breasts are classified according to the mammary gland content rate (hereinafter, referred to as a "mammary gland content rate in the breast") of the entire breast region and the mammary gland content rate in the mammary gland concentrated region as another example of the classification corresponding to the mammary gland content rate. In the example illustrated in FIG. 7, categories I to IV are given according to a combination of the mammary gland content rate in the breast and the mammary gland content rate in the mammary gland concentrated region. As a value indicating the category becomes larger, the object of interest is more difficult to see. Even in a case in which the mammary gland content rate in the breast is low, if the mammary gland content rate in the mammary gland concentrated region is high, the object of interest is likely to be hidden by the mammary gland concentrated region 66 and is difficult to see. Therefore, in the example illustrated in FIG. 7, in a case in which the mammary gland content rate in the mammary gland concentrated region is high regardless of the mammary gland content rate in the breast, the object of interest falls into the category (IV) with a large value.

In the case in which the classification illustrated in FIG. 7 is applied, the mammary gland content rate in the breast derived in Step S152 is derived in this step. Therefore, the process in Step S152 is omitted.

Then, in Step S152, the control unit 40 derives the mammary gland content rate in the breast. Specifically, the control unit 40 derives the representative value of the mammary gland content rate in the breast region 54 as the mammary gland content rate in the breast on the basis of the pixel unit mammary gland content rate map obtained in Step S104 of the mammary gland concentrated region detection process.

Then, in Step S154, the control unit 40 determines whether the selection of the mammary gland content rate to be displayed on the display unit 46 has been received. The console 6 according to this embodiment is configured such that the user can select the mammary gland content rate to be displayed on the display unit 46 from the mammary gland content rate in the mammary gland concentrated region and the mammary gland content rate in the breast through the operation unit 48. Therefore, the control unit 40 determines whether the selection of a display target has been received. In a case in which the selection of the display target has been received through the operation unit 48, the determination result in Step S154 is "Yes" and the process proceeds to Step S156.

In Step S156, the control unit 40 displays a mammary gland concentrated region highlighted image (which will be described in detail below) in which the mammary gland concentrated region 66 has been highlighted, the radiographic image of the breast, and the selected mammary gland content rate (at least one of the mammary gland content rate in the mammary gland concentrated region or the mammary gland content rate in the breast) on the display unit 46 and then proceeds to Step S160.

On the other hand, in a case in which the selection of the display target has not been received through the operation unit 48, the determination result in Step S154 is "No" and the process proceeds to Step S158.

Figure 8A:
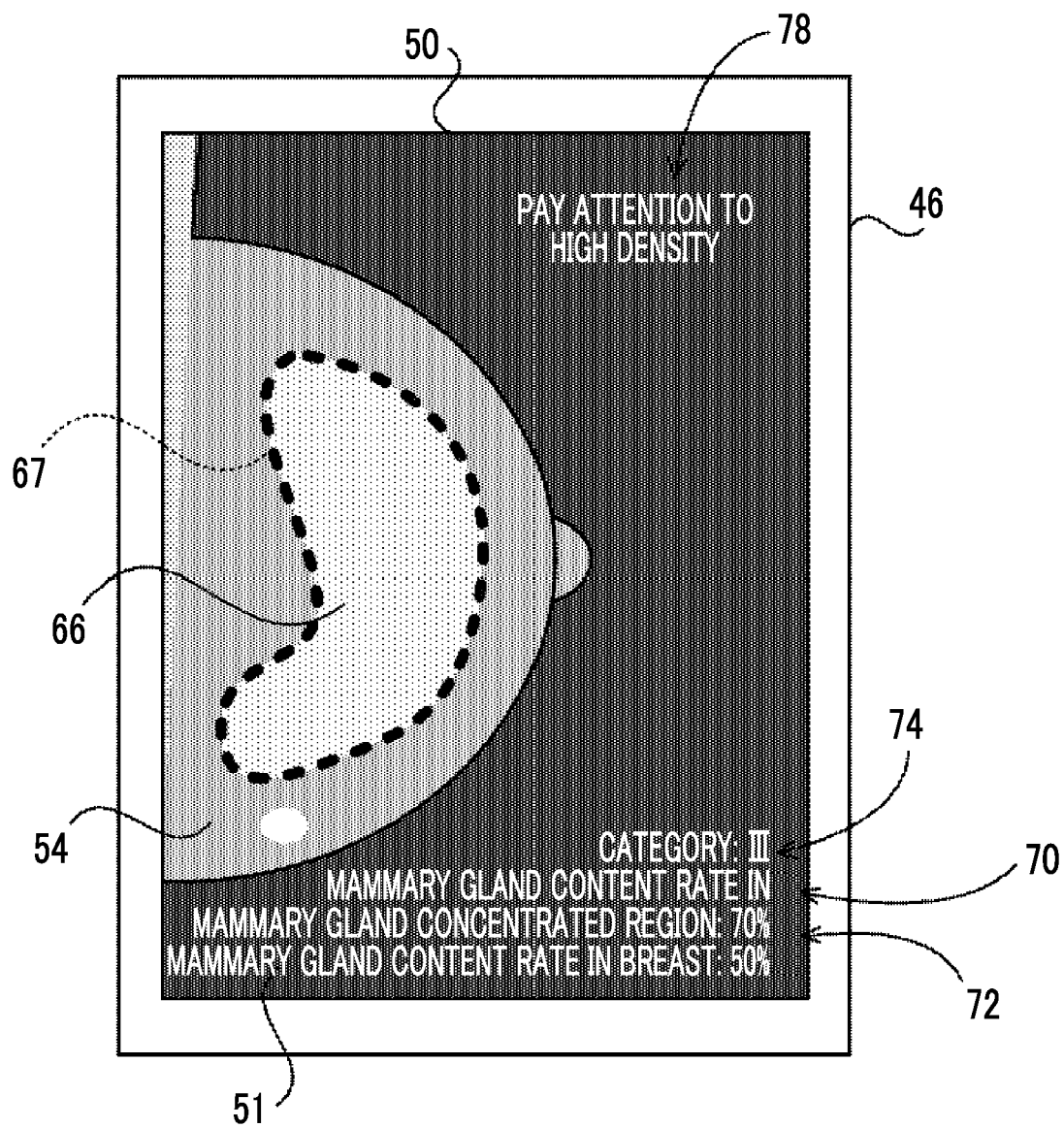
FIG. 8A is a diagram illustrating an example of a mammary gland concentrated region highlighted image, a radiographic image of the breast, the mammary gland content rate in the mammary gland concentrated region, and the mammary gland content rate in the breast displayed on a display unit by the console in the first embodiment.

Then, in Step S158, the control unit 40 displays the mammary gland concentrated region highlighted image, the radiographic image of the breast, the mammary gland content rate in the mammary gland concentrated region, and the mammary gland content rate in the breast on the display unit 46 and then proceeds to Step S160. FIG. 8A illustrates an example in which the control unit 40 displays the mammary gland concentrated region highlighted image, the radiographic image of the breast, the mammary gland content rate in the mammary gland concentrated region, and the mammary gland content rate in the breast on the display unit 46.

FIG. 8A illustrates an example of the display of an image, in which a boundary line 67 indicating the boundary between the mammary gland concentrated region 66 and other regions is superimposed on the radiographic image 50, as the mammary gland concentrated region highlighted image. The mammary gland concentrated region highlighted image is not particularly limited as long as the mammary gland concentrated region 66 is highlighted so as to be easily seen. For example, the mammary gland concentrated region highlighted image may be an image in which the color of the mammary gland concentrated region 66 is different from the colors of other parts. In addition, the mammary gland concentrated region highlighted image may be an image that masks (covers) the mammary gland concentrated region 66 and may be displayed side by side with the radiographic image 50 or may be displayed so as to be superimposed on the radiographic image 50.

FIG. 8A illustrates an example in which information 70 indicating the mammary gland content rate in the mammary gland concentrated region, information 72 indicating the mammary gland content rate in the breast, and information 74 indicating the category specified in Step S150 are displayed in the directly irradiated region 51 of the radiographic image 50.

In Step S160, the control unit 40 determines whether the mammary gland content rate in the mammary gland concentrated region is equal to or greater than a warning threshold value determined for warning. In a case in which the mammary gland content rate in the mammary gland concentrated region is less than the warning threshold value, the determination result in Step S160 is "No" and the radiographic image display process ends. On the other hand, in a case in which the mammary gland content rate in the mammary gland concentrated region is equal to or greater than the warning threshold value, the determination result in Step S160 is "Yes" and the process proceeds to Step S162.

The warning threshold value is a threshold value for determining whether to warn the user that the object of interest is difficult to see, that is, the density of the mammary glands is high since the mammary gland content rate is high. The warning threshold value may be predetermined according to, for example, category classification or may be set and change by, for example, the user through the operation unit 48.

In Step S162, the control unit 40 displays information indicating a predetermined warning on the display unit 46 and then ends the radiographic image display process. FIG. 8A illustrates an example in which information 78 indicating a warning is displayed in the directly irradiated region 51 of the radiographic image 50.

The aspect in which, in Step S150 of the radiographic image display process, the control unit 40 specifies the category (hereinafter, referred to as a "first category"), to which the breast which is an object belongs, on the basis of the mammary gland content rate in the mammary gland concentrated region. However, the specification of the category to which the breast belongs is not limited to this embodiment. For example, the control unit 40 may specify the category (hereinafter, referred to as a "second category"), to which the breast belongs, on the basis of the mammary gland content rate in the breast instead of the first category or in addition to the first category.

The control unit 40 may determine which of the first category and the second category is specified and displayed on the display unit 46 in advance. In addition, for example, a configuration in which the user can select which of the first category and the second category is specified and displayed on the display unit 46, using the operation unit 48, may be used as in the aspect in which the user can select the display target.

A method for specifying the second category in the control unit 40 is not particularly limited and may be the same as, for example, the method for specifying the first category. For example, a category corresponding to the mammary gland content rate in the breast may be specified using the example of the categories into which the breasts are classified according to the mammary gland content rate illustrated in FIG. 6.

Figure 8B:
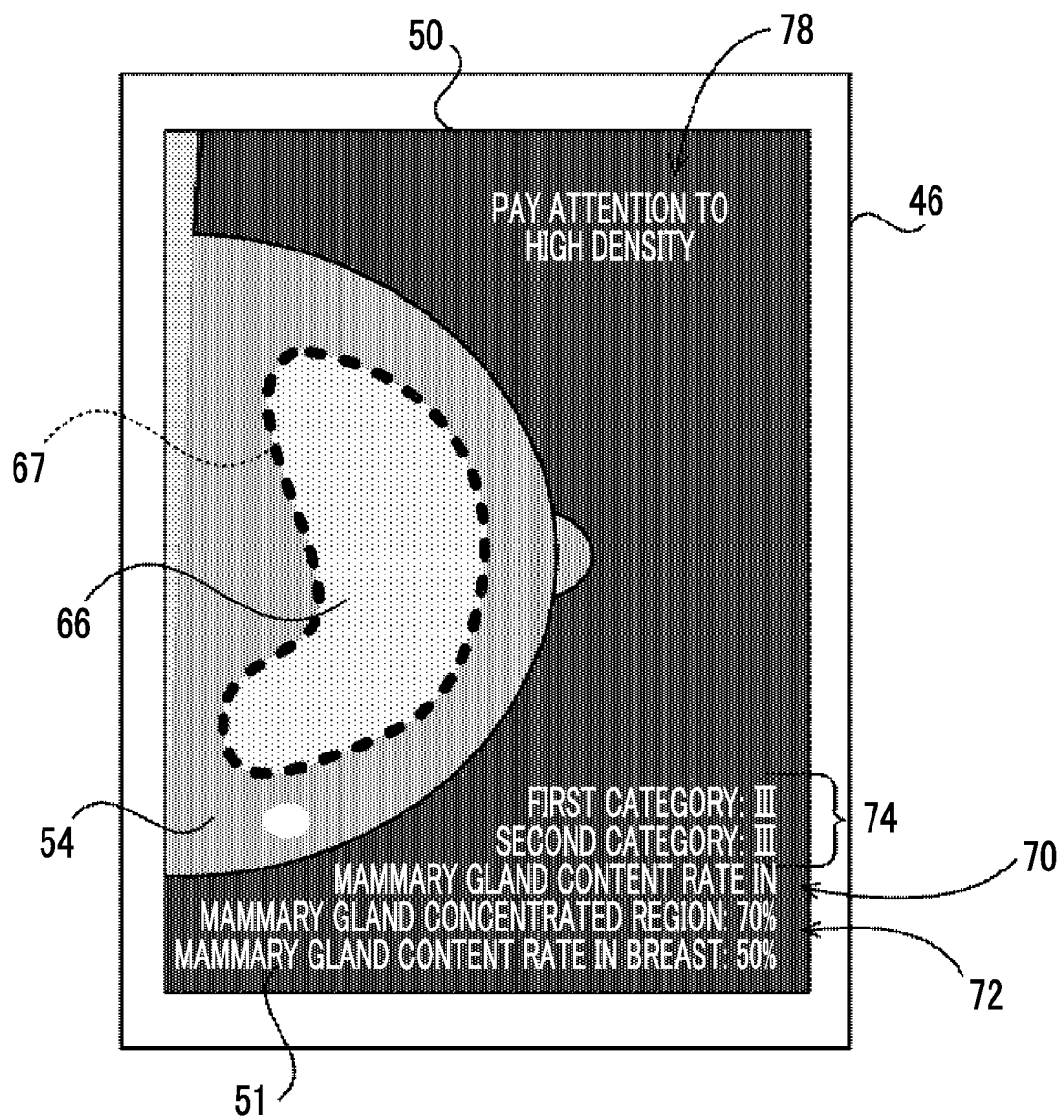
FIG. 8B is a diagram illustrating another example of the mammary gland concentrated region highlighted image, the radiographic image of the breast, the mammary gland content rate in the mammary gland concentrated region, and the mammary gland content rate in the breast displayed on the display unit by the console in the first embodiment.

In this case, the control unit 40 displays the category (at least one of the first category or the second category) specified in Step S150 on the display unit 46 in Step S156 or Step S158. FIG. 8B illustrates an example in which the control unit 40 displays information 74 indicating both the first category and the second category on the display unit 46, in addition to the mammary gland concentrated region highlighted image, the radiographic image of the breast, the mammary gland content rate in the mammary gland concentrated region, and the mammary gland content rate in the breast.

Figure 9:
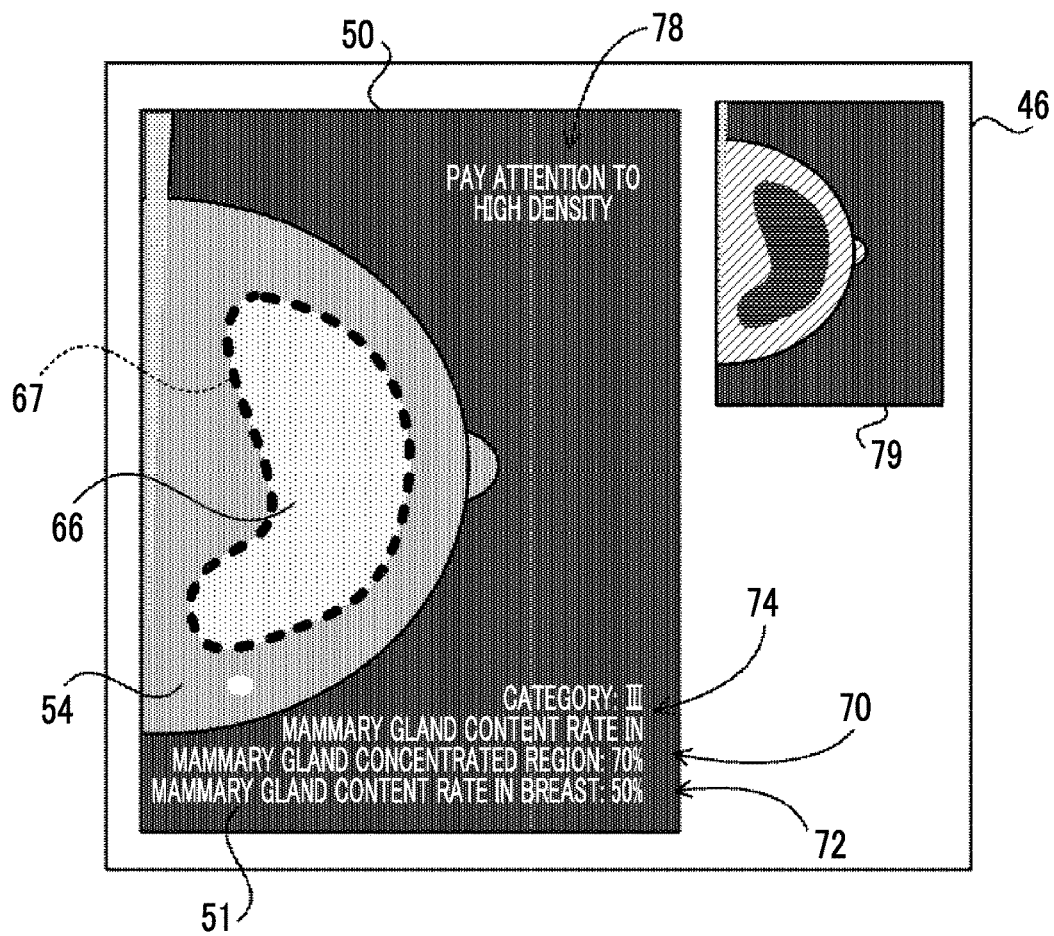
FIG. 9 is a diagram illustrating an example of the mammary gland concentrated region highlighted image, the radiographic image of the breast, the mammary gland content rate in the mammary gland concentrated region, the mammary gland content rate in the breast, and a pixel unit mammary gland content rate map displayed on the display unit by the console in the first embodiment.

The information displayed on the display unit 46 by the radiographic image display process is not limited to the above-mentioned information. For example, FIG. 9 illustrates an example of a state in which the mammary gland concentrated region highlighted image, the radiographic image of the breast, the mammary gland content rate in the mammary gland concentrated region, the mammary gland content rate in the breast, and a pixel unit mammary gland content rate map 79 are displayed on the display unit 46. As illustrated in FIG. 9, for example, the pixel unit mammary gland content rate map 79 or the local unit mammary gland content rate map may be displayed as information indicating the mammary gland content rate for each pixel of the breast region 54 on the display unit 46, in addition to the above-mentioned information or instead of the above-mentioned information.

Figure 10:
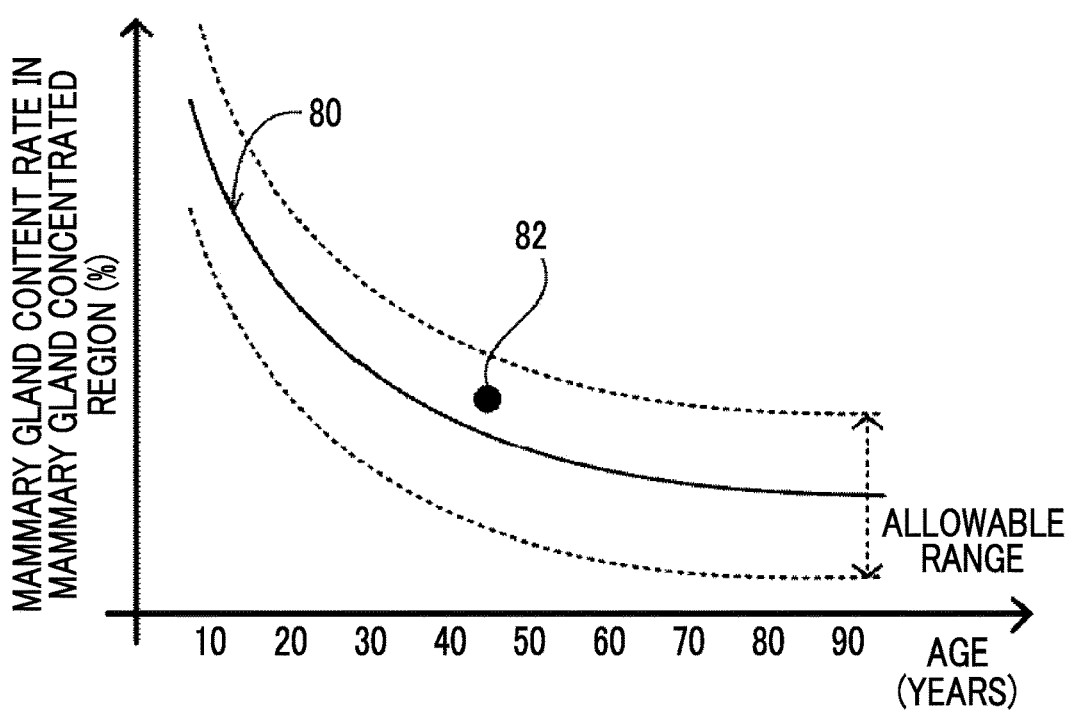
FIG. 10 is a diagram illustrating an example of the result of comparison between statistical data and the mammary gland content rate in the mammary gland concentrated region derived in the mammary gland concentrated region detection process.

In a case in which statistical data indicating the correspondence relationship between at least one of the age of the subject or the thickness of the breast (the thickness in a state in which the breast is compressed by the compression plate 20 in imaging by the mammography apparatus 10) and the mammary gland content rate in the mammary gland concentrated region is obtained, the control unit 40 may display the result of comparison between the statistical data and the mammary gland content rate in the mammary gland concentrated region derived in the mammary gland concentrated region detection process on the display unit 46. FIG. 10 illustrates an example of the comparison result. FIG. 10 illustrates a state in which a mark 82 indicating the derived mammary gland content rate in the mammary gland concentrated region is superimposed on a graph 80 indicating the average value of the mammary gland content rate in the mammary gland concentrated region for each age as the statistical data indicating the correspondence relationship between the age and the mammary gland content rate in the mammary gland concentrated region. In addition, in the example illustrated in FIG. 10, an allowable range of the mammary gland content rate in the mammary gland concentrated region may be determined on the basis of the average value and warning may be performed in a case in which the derived mammary gland content rate in the mammary gland concentrated region is out of the allowable range.

As such, in the console 6 according to this embodiment, the control unit 40 functions as an acquisition unit that acquires a radiographic image of the breast, a derivation unit that derives the mammary gland content rate for each pixel of the breast region 54 in the radiographic image, and a detection unit that detects the mammary gland concentrated region 66 on the basis of the result of specifying whether or not the specific pixel 60, which is each pixel of the breast region 54, is a pixel included in the mammary gland concentrated region 66 in which the mammary glands are concentrated in the breast region 54 on the basis of the mammary gland content rate of the specific pixel 60 and the mammary gland content rate of pixels in the local region 62 around the specific pixel 60.

That is, the console 6 according to this embodiment detects the mammary gland concentrated region 66, considering the mammary gland content rate of the pixels around the specific pixel 60.

Therefore, according to the console 6 of this embodiment, it is possible to detect the mammary gland concentrated region 66 in which the object of interest needs to be carefully observed in the radiographic image 50 of the breast.

Second Embodiment

Next, a second embodiment will be described in detail. In this embodiment, the same configurations and operations as those in the first embodiment are denoted by the same reference numerals and the detailed description thereof will not be repeated.

Since the configurations of a radiography system 1, a console 6, and a mammography apparatus 10 are the same as those in the first embodiment, the description thereof will not be repeated. In this embodiment, since a mammary gland concentrated region detection process performed by the control unit 40 of the console 6 is partially different from the mammary gland concentrated region detection process (see FIG. 3) in the first embodiment, different processes will be described.

Figure 11:
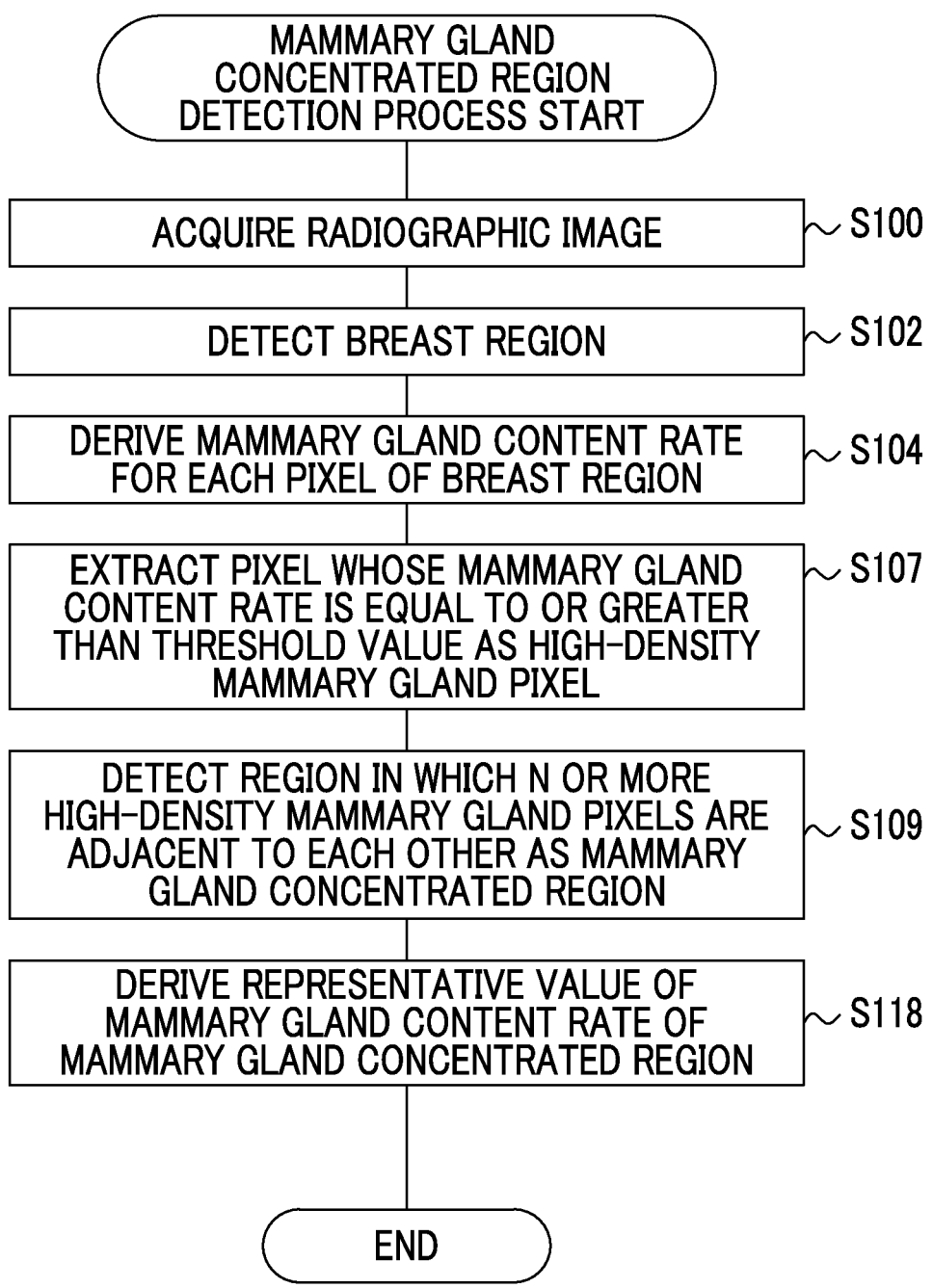
FIG. 11 is a flowchart illustrating an example of the flow of a mammary gland concentrated region detection process performed by a console according to a second embodiment.

FIG. 11 is a flowchart illustrating an example of the flow of the mammary gland concentrated region detection process in the console 6 according to this embodiment. In a case in which the mammary gland concentrated region detection process illustrated in FIG. 11 is performed, the control unit 40 functions as an example of an acquisition unit, a derivation unit, and a detection unit according to the present disclosure.

The mammary gland concentrated region detection process illustrated in FIG. 11 differs from the mammary gland concentrated region detection process (see FIG. 3) according to the first embodiment in that a process in Steps S107 and S109 is performed instead of the process in Steps S106 to S116. Therefore, different processes will be described.

In Step S107, the control unit 40 extracts a pixel whose mammary gland content rate is equal to or greater than a threshold value among the pixels of the breast region 54 as a high-density mammary gland pixel.

Then, in Step S109, the control unit 40 detects a region in which n or more extracted high-density mammary gland pixels are adjacent to each other as the mammary gland concentrated region 66. Preferably, n which is the number of high-density mammary gland pixels adjacent to each other and is used to determine whether the mammary gland concentrated region 66 is present is an integer that is equal to or greater than 0 and is greater than the number of pixels included in the local region 62 according to the first embodiment. A specific value may be predetermined according to the size of the object of interest to be observed or may be set and changed by, for example, the user through the operation unit 48.

Since a radiographic image display process performed after the mammary gland concentrated region detection process is the same as the radiographic image display process (see FIG. 5) according to the first embodiment, the description thereof will not be repeated.

As such, in the console 6 according to this embodiment, the control unit 40 functions as an acquisition unit that acquires a radiographic image of the breast, a derivation unit that derives the mammary gland content rate for each pixel of the breast region 54 in the radiographic image, and a detection unit that detects a region in which a predetermined number or more of pixels whose mammary gland content rate is equal to or greater than a predetermined threshold value are adjacent to each other as the mammary gland concentrated region 66 in which the mammary glands are concentrated in the breast region 54.

That is, the console 6 according to this embodiment detects the region including a predetermined number or more of pixels whose mammary gland content rate is equal to or greater than the predetermined threshold value as the mammary gland concentrated region 66, also considering the mammary gland content rate of surrounding pixels.

Therefore, according to the console 6 of this embodiment, it is possible to detect the mammary gland concentrated region 66 in which the object of interest needs to be carefully observed in the radiographic image 50 of the breast.

Third Embodiment

Next, a third embodiment will be described in detail. In this embodiment, the same configurations and operations as those in the first embodiment are denoted by the same reference numerals and the detailed description thereof will not be repeated.

Since the configurations of a radiography system 1 and a console 6 are the same as those in the first embodiment, the description thereof will not be repeated. In this embodiment, the configuration of a mammography apparatus 10 is partially different from that in the first embodiment. The mammography apparatus 10 according to this embodiment has a so-called tomosynthesis imaging function which irradiates the breast with the radiation R emitted from the radiation source 29 at each of a plurality of irradiation angles to capture a plurality of projection images.

Figure 12:
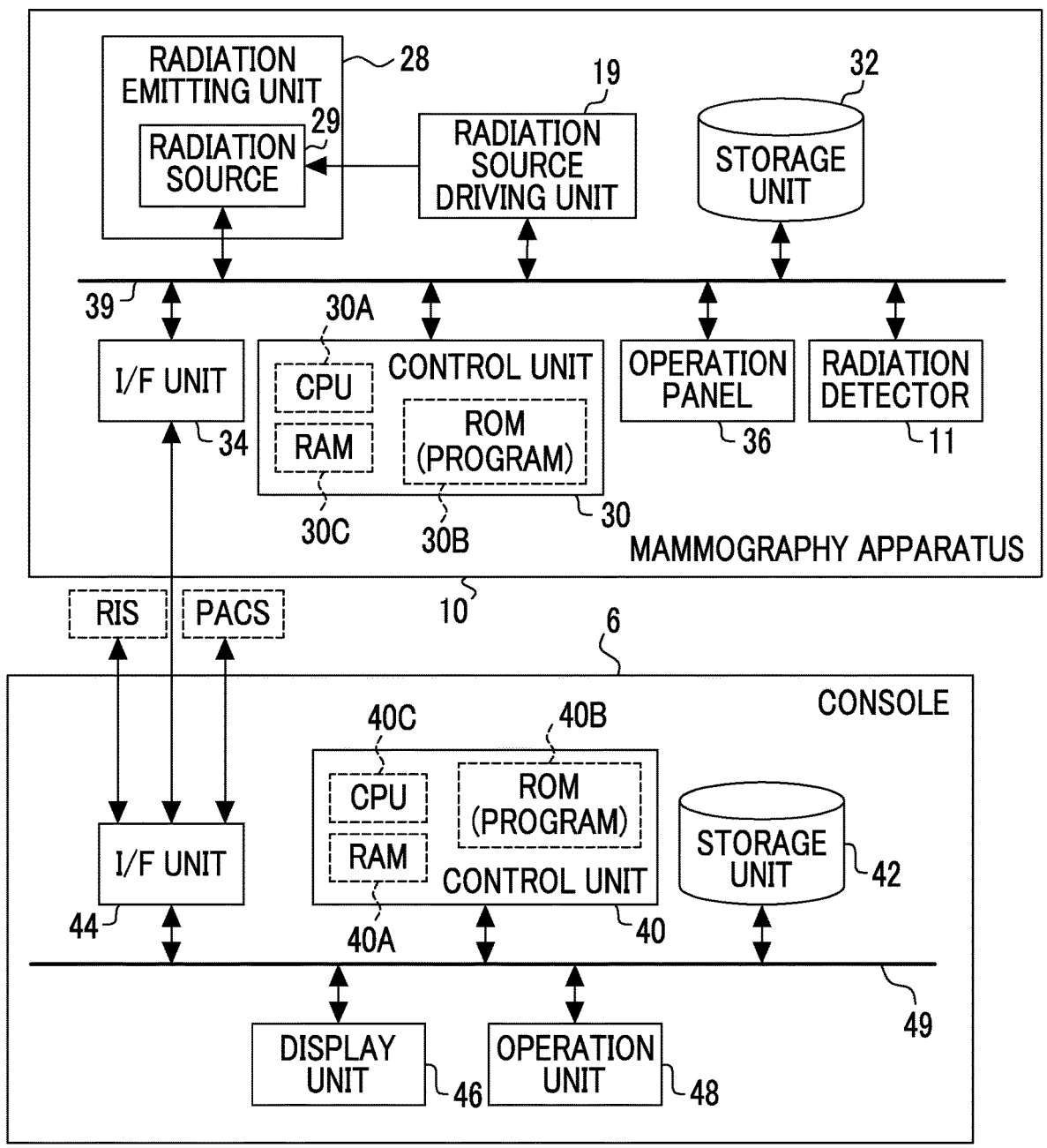
FIG. 12 is a block diagram illustrating an example of the configuration of a console and a mammography apparatus according to a third embodiment.
Figure 13:
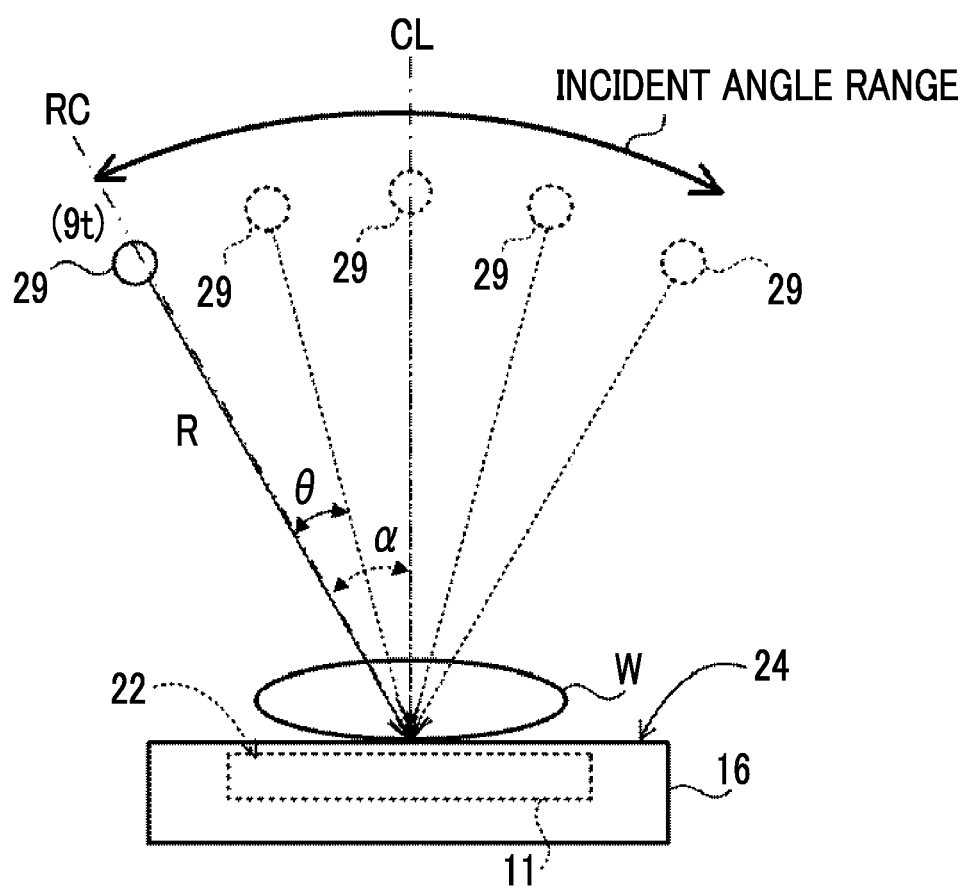
FIG. 13 is a diagram illustrating tomosynthesis imaging performed by the mammography apparatus according to the third embodiment.

FIG. 12 is a block diagram illustrating an example of the configuration of the console 6 and the mammography apparatus 10 according to this embodiment. As illustrated in FIG. 12, the mammography apparatus 10 according to this embodiment differs from the mammography apparatus 10 (see FIG. 2) according to the first embodiment in that it further comprises a radiation source driving unit 19 which moves the radiation source 29 to a plurality of positions with different irradiation angles. FIG. 13 is a diagram illustrating tomosynthesis imaging performed by the mammography apparatus 10 according to this embodiment.

In a case in which the mammography apparatus 10 performs the tomosynthesis imaging, the radiation source driving unit 19 continuously moves the radiation source 29 of the radiation emitting unit 28 to each of the plurality of irradiation positions with different irradiation angles (projection angles). In this embodiment, as illustrated in FIG. 13, the radiation source 29 is moved to irradiation positions 9$t$ (t=0, 1, . . . , T; T=5 in FIG. 13) where irradiation angles are different from each other and which are spaced a predetermined angle θ apart, that is, the positions where the incident angles of the radiation R with respect to a detection surface 22 of the radiation detector 11 are different from each other. At each irradiation position, a breast W is irradiated with the radiation R from the radiation source 29 in response to a command from the console 6 and the radiation detector 11 captures a radiographic image. In this embodiment, in the tomosynthesis imaging, the radiographic images captured by the radiation detector 11 at the plurality of irradiation positions with different irradiation angles are referred to as "projection images". In a case in which the mammography apparatus 10 performs the tomosynthesis imaging which moves the radiation source 29 to each of the irradiation positions 9$t$ and captures the projection image at each of the irradiation positions 9$t$, T projection images are obtained.

As illustrated in FIG. 13, the incident angle of the radiation R means an angle α formed between a normal line CL to the detection surface 22 of the radiation detector 11 and a radiation axis RC. Here, it is assumed that the detection surface 22 of the radiation detector 11 is substantially parallel to the imaging surface 24. Hereinafter, as illustrated in FIG. 13, a predetermined range in which the incident angles are different from each other in the tomosynthesis imaging is referred to as an "incident angle range". A specific example of the incident angle range is a range of ±10 degrees or ±20 degrees with respect to the normal line CL to the detection surface 22 of the radiation detector 11.

In contrast, in a case in which the mammography apparatus 10 performs simple imaging, the radiation source 29 remains fixed at an irradiation position (an irradiation position along a normal direction) with an irradiation angle α of 0 degrees. The radiation source 29 emits the radiation R in response to a command from the console 6 and the radiation detector 11 captures a radiographic image. In this embodiment, the radiographic image captured by the radiation detector 11 in the simple imaging is referred to as a "two-dimensional image".

Next, the operation of the console 6 according to this embodiment will be described. The console 6 according to this embodiment has a function of performing the tomosynthesis imaging in addition to capturing the two-dimensional image in a case in which the mammary gland content rate in the mammary gland concentrated region is equal to or greater than a threshold value.

Figure 14:
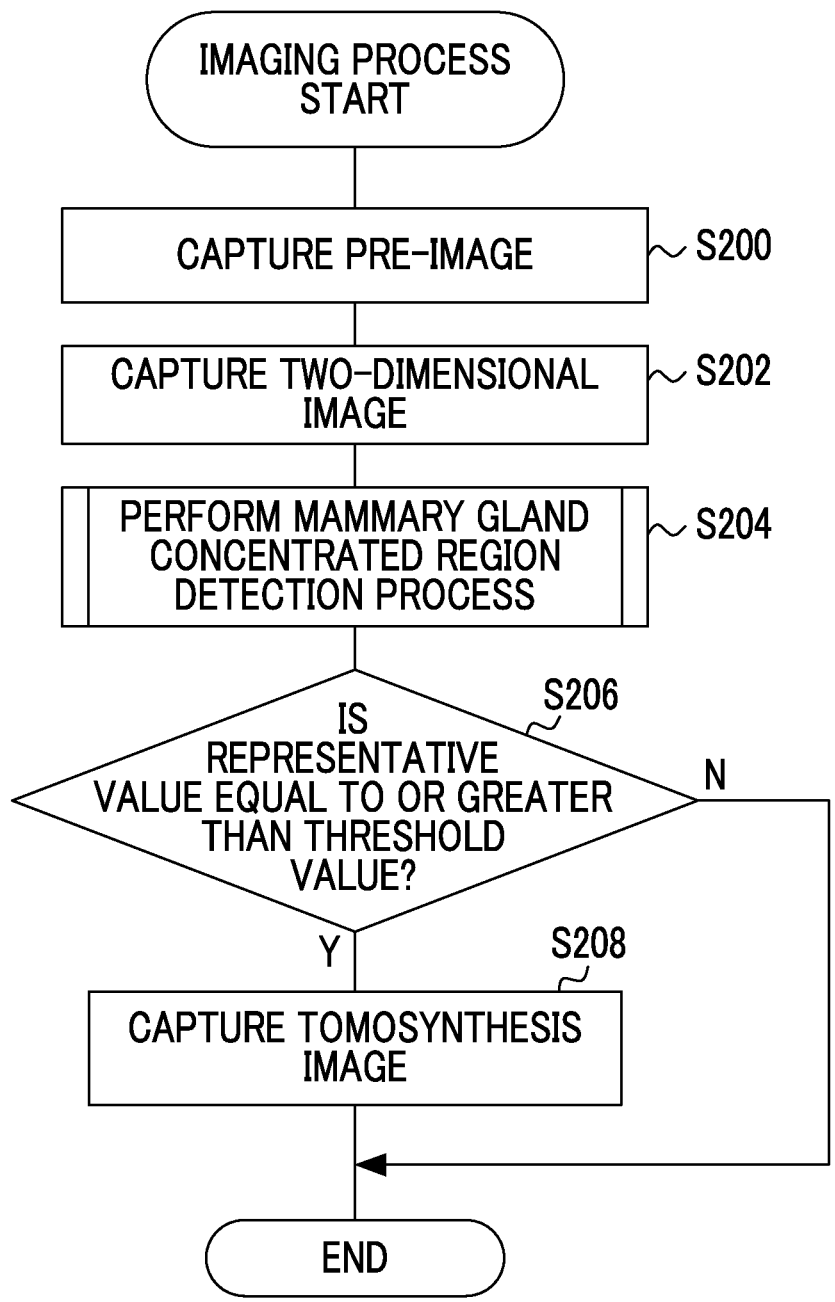
FIG. 14 is a flowchart illustrating an example of the flow of an imaging process performed by the console according to the third embodiment.

For example, the console 6 according to this embodiment performs an imaging process in a case in which a command to capture a radiographic image is received from the user through the operation unit 48 of the console 6. FIG. 14 is a flowchart illustrating an example of the flow of the imaging process performed by the control unit 40 of the console 6 according to this embodiment.

For example, in a case in which the console 6 according to this embodiment receives a command to display a radiographic image from the user through the operation unit 48 of the console 6, the CPU 40A of the control unit 40 executes an imaging processing program stored in the ROM 40B to perform an imaging process illustrated in FIG. 14. In a case in which the imaging process is performed, the control unit 40 functions as an example of an acquisition unit, a derivation unit, a detection unit, and a commanding unit according to the present disclosure.

In Step S200 illustrated in FIG. 14, the control unit 40 directs the mammography apparatus 10 to emit the radiation R whose amount is significantly less than that in normal imaging to capture a radiographic image before a two-dimensional image is captured. In this embodiment, the radiographic image obtained by this imaging process is referred to as a "pre-image" so as to be distinguished from the radiographic image obtained by normal imaging. In some cases, the pre-image is used to check, for example, the positioning of the subject.

Then, in Step S202, in a case in which the mammography apparatus 10 ends the capture of the pre-image, the control unit 40 directs the mammography apparatus 10 to continuously capture the two-dimensional image of the breast.

Then, in Step S204, the control unit 40 performs a mammary gland concentrated region detection process. The mammary gland concentrated region detection process performed in this step is the same as the mammary gland concentrated region detection process (see FIGS. 3 and 11) described in each of the above-described embodiments except that the pre-image captured by the mammography apparatus 10 is acquired according to the process in Step S200. In addition, the mammary gland concentrated region detection process of the control unit 40 is performed in parallel to the capture of the two-dimensional image by the mammography apparatus 10.

The mammary gland concentrated region detection process is performed to detect the mammary gland concentrated region 66 from the breast region 54 of the pre-image and to derive the mammary gland content rate in the mammary gland concentrated region as the representative value of the mammary gland content rate of the mammary gland concentrated region 66.

Then, in Step 206, the control unit 40 determines whether the mammary gland content rate in the mammary gland concentrated region is equal to or greater than a threshold value. The threshold value used in this determination process may be predetermined or may be set and changed by, for example, the user through the operation unit 48. In a case in which the mammary gland content rate in the mammary gland concentrated region is not equal to or greater than the threshold value, that is, in a case in which the mammary gland content rate in the mammary gland concentrated region is less than the threshold value, the determination result in Step S206 is "No" and the control unit 40 ends the imaging process. On the other hand, in a case in which the mammary gland content rate in the mammary gland concentrated region is equal to or greater than the threshold value, the determination result in Step S206 is "Yes" and the control unit 40 proceeds to Step S208.

In Step S208, the control unit 40 directs the mammography apparatus 10 to perform the tomosynthesis imaging and then ends the imaging process.

As such, in a case in which it is presumed that the object of interest is difficult to see according to the mammary gland content rate in the mammary gland concentrated region detected from the pre-image captured before the two-dimensional image is captured, the console 6 according to this embodiment directs the mammography apparatus 10 to perform the tomosynthesis imaging.

Therefore, according to this embodiment, it is possible to generate a tomographic image from the projection images and to display the tomographic image on the display unit 46. Therefore, the interpretation of the two-dimensional image can be assisted by the tomographic image and the object of interest can be easily seen.

In addition, a method for displaying the tomographic image generated from the projection images obtained by the tomosynthesis imaging in the console 6 according to this embodiment in a case in which the tomosynthesis imaging is performed in response to a command from, for example, the user will be described.

Figure 15:
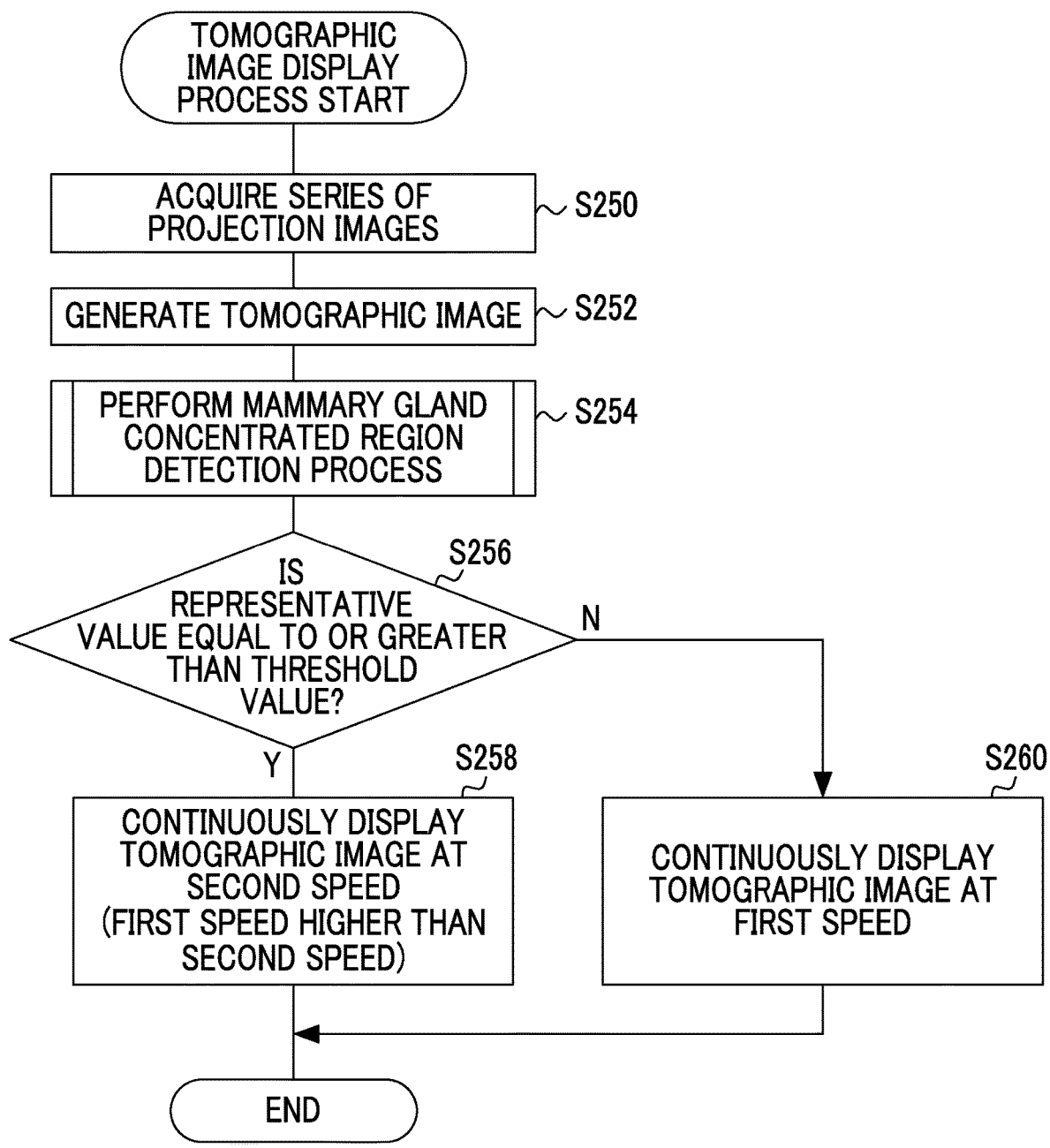
FIG. 15 is a flowchart illustrating an example of the flow of a tomographic image display process performed by the console according to the third embodiment.

FIG. 15 is a flowchart illustrating an example of the flow of a tomographic image display process performed by the control unit 40 of the console 6 according to this embodiment.

For example, in a case in which the console 6 according to this embodiment receives a command to display a tomographic image from the user through the operation unit 48 of the console 6, the CPU 40A of the control unit 40 executes a tomographic image display processing program stored in the ROM 40B to perform the tomographic image display process illustrated in FIG. 15. In a case in which the tomographic image display process is performed, the control unit 40 functions as an example of an acquisition unit, a derivation unit, a detection unit, a generation unit, and a display speed control unit according to the present disclosure.

In Step S250 illustrated in FIG. 15, the control unit 40 acquires a series of projection images captured by the tomosynthesis imaging.

Then, in Step S252, the control unit 40 generates a tomographic image with any slice thickness from the series of projection images. A method for generating the tomographic image is not particularly limited. A known reconstruction processing method, such as a filter back projection (FBP) method or an iterative reconstruction method, can be applied.

Then, in Step S254, the control unit 40 performs a mammary gland concentrated region detection process. The mammary gland concentrated region detection process in this step is the same as the mammary gland concentrated region detection process (see FIGS. 3 and 11) described in each of the above-described embodiments. In addition, the radiographic image from which the mammary gland concentrated region 66 is to be detected is not particularly limited and may be, for example, a projection image selected from the series of projection images or a two-dimensional image generated from the tomographic image.

The mammary gland concentrated region detection process is performed to detect the mammary gland concentrated region 66 and to derive the mammary gland content rate in the mammary gland concentrated region as the representative value of the mammary gland content rate of the mammary gland concentrated region 66.

Then, in Step 256, the control unit 40 determines whether the mammary gland content rate in the mammary gland concentrated region is equal to or greater than a threshold value. The threshold value used in this determination process may be predetermined or may be set and changed by, for example, the user through the operation unit 48. In a case in which the mammary gland content rate in the mammary gland concentrated region is not equal to or greater than the threshold value, that is, in a case in which the mammary gland content rate in the mammary gland concentrated region is less than the threshold value, the determination result in Step S256 is "No" and the control unit 40 proceeds to Step S260.

In Step S260, the control unit 40 sequentially and continuously displays the generated tomographic images on the display unit 46 according to a slice position at a predetermined first speed and then ends the tomographic image display process.

On the other hand, in a case in which the mammary gland content rate in the mammary gland concentrated region is equal to or greater than the threshold value, the determination result in Step S256 is "Yes" and the control unit 40 proceeds to Step S258. In Step S258, the control unit 40 sequentially and continuously displays the generated tomographic images on the display unit 46 according to a slice position at a second speed lower than the predetermined first speed and then ends the tomographic image display process.

As such, in this embodiment, in a case in which it is presumed that the object of interest is difficult to see according to the detected mammary gland content rate in the mammary gland concentrated region, the display speed of the tomographic image is lower than usual. Therefore, according to this embodiment, the object of interest can be easily seen.

In each of the above-described embodiments, the aspect in which the statistics of the mammary gland content rate in the mammary gland concentrated region is used as the representative value of the mammary gland content rate of the mammary gland concentrated region 66 has been described. However, values other than the statistics may be used. For example, the volume ratio of the mammary gland tissues may be used.

Figure 16:
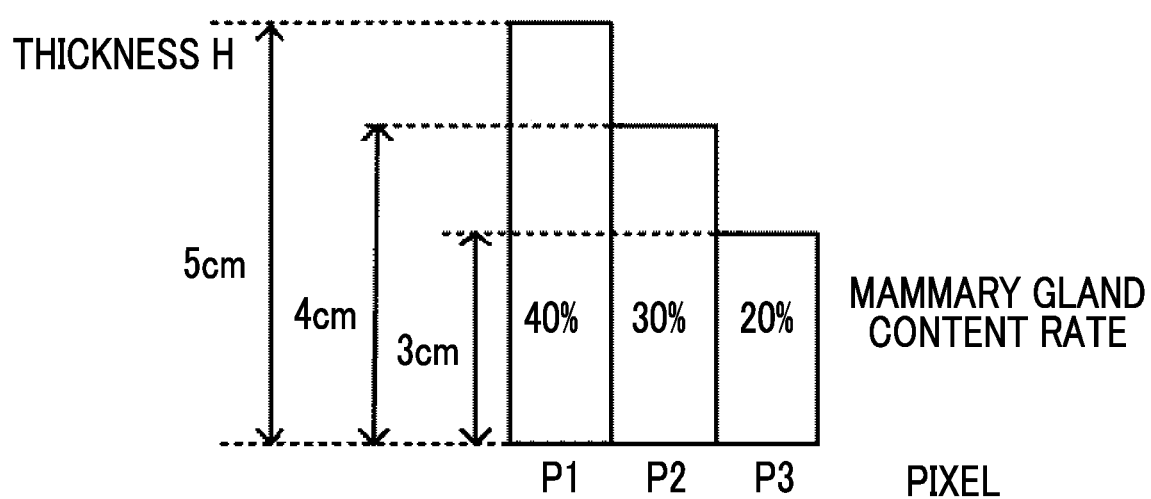
FIG. 16 is a diagram schematically illustrating a volume ratio of mammary gland tissues.

In a case in which the thickness of the breast in the mammary gland concentrated region 66 is constant, the volume ratio is equal to an average value. However, for example, in some cases, the thickness of the breast is not constant in a case in which a peripheral portion of the breast is rounded and the thickness of the breast is changed or in a case in which the compression plate 20 is inclined. In a case in which the thickness of the breast is not constant, the volume ratio may be different from the average value. For example, as schematically illustrated in FIG. 16, it is assumed that the mammary gland concentrated region 66 includes three pixel regions P1 to P3, the thickness H of the pixel region P1 is 5 cm, the mammary gland content rate of the pixel region P1 is 40%, the thickness H of the pixel region P2 is 4 cm, the mammary gland content rate of the pixel region P2 is 30%, the thickness H of the pixel region P3 is 3 cm, and the mammary gland content rate of the pixel region P3 is 20. The average value of the mammary gland content rates of the pixel regions P1 to P3 is (40+30+20)/3=30%. In contrast, the volume ratio of the mammary gland tissues (mammary gland content rates) of the pixel regions P1 to P3 is (5×40+4×30+3×20)/(5+4+3)≈32% and is different from the average value. Therefore, in some cases, the volume ratio is more preferably used than the average value.

In a case in which the volume ratio is used, in Step S118 of the mammary gland concentrated region detection process (see FIG. 3), the control unit 40 derives the volume ratio as the representative value of the mammary gland content rate of the mammary gland concentrated region 66. The volume ratio can be derived on the basis of, for example, the mammary gland content rate of each pixel and the thickness of the breast corresponding to each pixel. A specific derivation method is not particularly limited and a known method can be applied. For example, the control unit 40 acquires a height (a gap between the compression plate 20 and the imaging surface 24) T from the imaging surface 24 of the compression plate 20 in a state in which the breast is compressed, models the peripheral portion of the breast in a semicircular shape, and derives the thickness H of the breast according to the distance from the periphery of the breast in the radiographic image, using the following Expression (2):

$$H=2\times\sqrt{(T-X)\times X} \qquad (2).$$

In Expression (2), "X" is the distance from the periphery of the breast.

In each of the above-described embodiments, the aspect in which the mammary gland concentrated region 66 is detected from the radiographic image has been described. However, in a case in which the mammary gland content rate of the entire breast is low, the mammary gland concentrated region 66 may not be detected. In this case, the control unit 40 of the console 6 may notify that the mammary gland concentrated region 66 has not been detected, instead of deriving the mammary gland content rate in the mammary gland concentrated region.

In the first embodiment, the aspect in which the breasts are classified into categories according to difficulty in seeing the object of interest and the mammary gland content rate in the mammary gland concentrated region. However, the classification method is not particularly limited. As the size of the mammary gland concentrated region 66 becomes larger, it is more difficult to see the object of interest. Therefore, for example, the breasts may be classified into categories indicating that, as the size (the number of pixels) of the mammary gland concentrated region 66 becomes larger, it is more difficult to see the object of interest.

In each of the above-described embodiments, various processors other than the CPU may perform the mammary gland concentrated region detection process and the radiographic image display process performed by the execution of software (program) by the CPU. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the mammary gland concentrated region detection process and the radiographic image display process may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which various programs, such as the mammary gland concentrated region detection processing program and the radiographic image display processing program, stored in the control unit 30 of the mammography apparatus 10 and the control unit 40 of the console 6 are stored (installed) in the ROMs (30B and 40B) of the control unit 30 and the control unit 40 in advance has been described. However, the invention is not limited thereto. Each of various programs may be recorded on a recording medium, such as a compact disk read only memory (CD-ROM), a digital versatile disk read only memory (DVD-ROM), or a universal serial bus (USB) memory, and then provided. In addition, each of various programs may be downloaded from an external apparatus through the network.

In each of the above-described embodiments, the radiation R is not particularly limited. For example, X-rays or γ-rays may be applied.

In addition, for example, the configuration and operation of the radiography system 1, the console 6, and the mammography apparatus 10 according to each of the above-described embodiments are illustrative and may be changed according to the situation, without departing from the scope and spirit of the invention. In addition, the above-described embodiments may be appropriately combined with each other.

EXPLANATION OF REFERENCES

1: radiography system
6: console
9t: irradiation position
10: mammography apparatus
11: radiation detector
12: imaging unit
14: base portion
16: imaging table
18: holding portion
19: radiation source driving unit
20: compression plate
22: detection surface
24: imaging surface
28: radiation emitting unit
29: radiation source
30, 40: control unit
30A, 40A: CPU
30B, 40B: ROM
30C, 40C: RAM
32, 42: storage unit
34, 44: I/F unit
36: operation panel
39, 49: bus
46: display unit
48: operation unit
50: radiographic image
51: directly irradiated region
52: scanning line
53: boundary
54: breast region
55A to 55D: pixel
60, 60A to 60D: specific pixel
62, 62A to 62D: local region
66: mammary gland concentrated region
67: boundary line
70, 72, 74, 78: information 79: pixel unit mammary gland content rate map
80: graph
82: mark
CL: normal line
R: radiation
RC: radiation axis
W: breast
α, θ: angle

What is claimed is:

1. An image processing apparatus comprising:
a processor configured to:
acquire a radiographic image of a breast;
derive a mammary gland content rate for each pixel of a breast region in the radiographic image; and
detect a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel around the specific pixel,
wherein the processor is further configured to derive a representative value of a mammary gland content rate of a local region which includes the specific pixel and has a predetermined size smaller than that of the breast region and specifies the specific pixel, of which a representative value of the mammary gland content rate is equal to or greater than a predetermined threshold value, in the local region as a pixel included in the mammary gland concentrated region, and
wherein the size of the local region is determined according to a size of an object of interest to be observed and the size of the local region is larger than the size of the object of interest.

2. The image processing apparatus according to claim 1, wherein the processor is further configured to derive a representative value of a mammary gland content rate of the mammary gland concentrated region and outputs the representative value.

3. The image processing apparatus according to claim 1, wherein the processor is further configured to perform control such that a category corresponding to the breast is specified from categories into which the breasts are classified according to the mammary gland content rate on the basis of the representative value of the mammary gland content rate of the mammary gland concentrated region and is displayed on a display unit.

4. The image processing apparatus according to claim 1, wherein the processor is further configured to perform control such that a category corresponding to the breast is specified from categories into which the breasts are classified according to the mammary gland content rate of the entire breast region and the mammary gland content rate of the entire mammary gland concentrated region, on the basis of the representative value of the mammary gland content rate of the mammary gland concentrated region and the mammary gland content rate of the entire breast region and is displayed on a display unit.

5. The image processing apparatus according to claim 1, wherein the processor is further configured to perform control such that at least one of a first category which corresponds to the breast and is specified from categories into which the breasts are classified according to the mammary gland content rate on the basis of the representative value of the mammary gland content rate of the mammary gland concentrated region or a second category which corresponds to the breast and is specified from the categories into which the breasts are classified according to the mammary gland content rate on the basis of a mammary gland content rate of the entire breast region is displayed on a display unit.

6. The image processing apparatus according to claim 1, wherein the processor is further configured to perform control such that the mammary gland content rate of the entire breast region and the mammary gland content rate of the entire mammary gland concentrated region are displayed on a display unit.

7. The image processing apparatus according to claim 6, wherein the processor is further configured to
receive a selection of a mammary gland content rate to be displayed from the mammary gland content rate of the entire breast region and the mammary gland content rate of the entire mammary gland concentrated region; and
perform control such that at least one of the mammary gland content rate of the entire breast region or the mammary gland content rate of the entire mammary gland concentrated region is displayed in response to the received selection.

8. The image processing apparatus according to claim 1, wherein the processor is further configured to perform control such that a result of comparison between a statistical value indicating a correspondence relationship between at least one of age or a thickness of the breast and the mammary gland content rate and the representative value of the mammary gland content rate of the mammary gland concentrated region is displayed on a display unit.

9. The image processing apparatus according to claim 1, wherein the processor is further configured to perform control such that the mammary gland concentrated region detected by the detection unit is displayed on a display unit so as to be highlighted.

10. The image processing apparatus according to claim 9, wherein the processor is further configured to perform control such that information indicating the mammary gland content rate of each pixel of the breast region derived by the derivation unit is further displayed on the display unit.

11. The image processing apparatus according to claim 1, wherein the processor is further configured to issue a warning indicating that the mammary gland content rate of the breast region is high in a case in which the representative value of the mammary gland content rate of the mammary gland concentrated region is equal to or greater than a predetermined threshold value.

12. The image processing apparatus according to claim 1, wherein the radiographic image is a two-dimensional image that is captured by a radiation detector of a mammography apparatus, and
the processor is further configured to output, to the mammography apparatus, a command to irradiate the breast with radiation emitted from a radiation source at a plurality of different irradiation angles to capture a plurality of projection images in a case in which the mammary gland content rate of the entire mammary gland concentrated region is equal to or greater than a threshold value.

13. The image processing apparatus according to claim 1, wherein the radiographic image is a plurality of projection images captured by a mammography apparatus by irradiating the breast with radiation emitted from a radiation source at a plurality of different irradiation angles, or the plurality of projection images and a two-dimensional image of the breast captured by the mammography apparatus, and the processor is further configured to:

generate a series of tomographic images from the plurality of projection images;

perform control such that the series of tomographic images is continuously displayed on the display unit at a first speed in a case in which the mammary gland content rate of the entire mammary gland concentrated region is less than a threshold value; and perform control such that the series of tomographic images is continuously displayed on the display unit at a second speed lower than the first speed in a case in which the mammary gland content rate of the entire mammary gland concentrated region is equal to or greater than the threshold value.

14. An image processing method comprising:

acquiring a radiographic image of a breast;

deriving a mammary gland content rate for each pixel of a breast region in the radiographic image;

detecting a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel around the specific pixel; and deriving a representative value of a mammary gland content rate of a local region which includes the specific pixel and has a predetermined size smaller than that of the breast region and specifies the specific pixel, of which a representative value of the mammary gland content rate is equal to or greater than a predetermined threshold value, in the local region as a pixel included in the mammary gland concentrated region, wherein the size of the local region is determined according to a size of an object of interest to be observed and the size of the local region is larger than the size of the object of interest.

15. An image processing apparatus comprising:

a processor configured to:

acquire a radiographic image of a breast;

derive a mammary gland content rate for each pixel of a breast region in the radiographic image; and detect a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel around the specific pixel, wherein the radiographic image is a two-dimensional image that is captured by a radiation detector of a mammography apparatus, and wherein the processor is further configured to output, to the mammography apparatus, a command to irradiate the breast with radiation emitted from a radiation source at a plurality of different irradiation angles to capture a plurality of projection images in a case in which the mammary gland content rate of the entire mammary gland concentrated region is equal to or greater than a threshold value.

16. An image processing apparatus comprising:

a processor configured to:

acquire a radiographic image of a breast;

derive a mammary gland content rate for each pixel of a breast region in the radiographic image; and detect a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel around the specific pixel, wherein the radiographic image is a plurality of projection images captured by a mammography apparatus by irradiating the breast with radiation emitted from a radiation source at a plurality of different irradiation angles, or the plurality of projection images and a two-dimensional image of the breast captured by the mammography apparatus, and the processor is further configured to:

generate a series of tomographic images from the plurality of projection images;

perform control such that the series of tomographic images is continuously displayed on the display unit at a first speed in a case in which the mammary gland content rate of the entire mammary gland concentrated region is less than a threshold value; and perform control such that the series of tomographic images is continuously displayed on the display unit at a second speed lower than the first speed in a case in which the mammary gland content rate of the entire mammary gland concentrated region is equal to or greater than the threshold value.

17. An image processing method comprising:

acquiring a radiographic image of a breast, the radiographic image being a two-dimensional image captured by a radiation detector of a mammography apparatus;

deriving a mammary gland content rate for each pixel of a breast region in the radiographic image; and detecting a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel around the specific pixel and outputting, to the mammography apparatus, a command to irradiate the breast with radiation emitted from a radiation source at a plurality of different irradiation angles to capture a plurality of projection images in a case in which the mammary gland content rate of the entire mammary gland concentrated region is equal to or greater than a threshold value.

18. An image processing method comprising:

acquiring a radiographic image of a breast, the radiographic image being a plurality of projection images captured by a mammography apparatus by irradiating the breast with radiation emitted from a radiation source at a plurality of different irradiation angles, or the plurality of projection images and a two-dimensional image of the breast captured by the mammography apparatus, deriving a mammary gland content rate for each pixel of a breast region in the radiographic image;

detecting a mammary gland concentrated region in which mammary glands are concentrated on the basis of a result of specifying whether a specific pixel which is each pixel of the breast region is a pixel included in the mammary gland concentrated region of the breast region on the basis of the mammary gland content rate of the specific pixel and a mammary gland content rate of a pixel around the specific pixel;

generating a series of tomographic images from the plurality of projection images;

performing control such that the series of tomographic images is continuously displayed on the display unit at a first speed in a case in which the mammary gland content rate of the entire mammary gland concentrated region is less than a threshold value; and performing control such that the series of tomographic images is continuously displayed on the display unit at a second speed lower than the first speed in a case in which the mammary gland content rate of the entire mammary gland concentrated region is equal to or greater than the threshold value.

* * * * *